(12) United States Patent
Huguet et al.

US008106000B2

(10) Patent No.: US 8,106,000 B2
(45) Date of Patent: Jan. 31, 2012

(54) COLONIC DELIVERY OF ADSORBENTS

(75) Inventors: Helene-Celine Huguet, Paris (FR);
Elias Fattal, Paris (FR); Antoine Andremont, Malakoff (FR); Nicolas Tsapis, Paris (FR)

(73) Assignee: Da Volterra, Paris (FR)

( * ) Notice: Subject to any disclaimer, the term of this patent is extended or adjusted under 35 U.S.C. 154(b) by 629 days.

(21) Appl. No.: 11/920,713

(22) PCT Filed: May 18, 2006

(86) PCT No.: PCT/EP2006/005629
§ 371 (c)(1),
(2), (4) Date: Mar. 12, 2009

(87) PCT Pub. No.: WO2006/122835
PCT Pub. Date: Nov. 23, 2006

(65) Prior Publication Data
US 2009/0324568 A1    Dec. 31, 2009

Related U.S. Application Data

(60) Provisional application No. 60/682,074, filed on May 18, 2005.

(51) Int. Cl.
*A01N 61/00* (2006.01)
(52) U.S. Cl. ......................................................... 514/1
(58) Field of Classification Search ........................ None
See application file for complete search history.

(56) References Cited

U.S. PATENT DOCUMENTS

| | | | |
|---|---|---|---|
| 5,364,636 A | 11/1994 | Ochi | |
| 5,484,773 A | 1/1996 | Heerze et al. | |
| 5,929,051 A | 7/1999 | Ni et al. | |
| 6,632,454 B2 | 10/2003 | Beckert et al. | |
| 7,485,294 B2 | 2/2009 | Bourgeois et al. | |
| 2001/0051150 A1 | 12/2001 | Ranganathan et al. | |
| 2002/0187134 A1 | 12/2002 | Ranganathan et al. | |
| 2005/0186272 A1 | 8/2005 | Mattern et al. | |
| 2005/0249716 A1 | 11/2005 | Bourgeois et al. | |
| 2008/0031867 A1 | 2/2008 | Huguet | |
| 2009/0162339 A1 | 6/2009 | Bourgeois et al. | |

FOREIGN PATENT DOCUMENTS

| | | |
|---|---|---|
| CN | 1326745 A | 12/2001 |
| DE | 24 37 878 A | 2/1976 |
| DE | 24 37 878 A1 | 2/1976 |
| WO | 0018377 A1 | 4/2000 |
| WO | 0114367 A1 | 3/2001 |
| WO | 02/060415 A1 | 8/2002 |
| WO | 03/032958 A1 | 4/2003 |
| WO | 03075852 A2 | 9/2003 |
| WO | 03/080032 A2 | 10/2003 |
| WO | 03086344 A1 | 10/2003 |
| WO | WO-03/103699 A1 | 12/2003 |
| WO | 2004012509 A1 | 2/2004 |
| WO | 2004012713 A1 | 2/2004 |
| WO | 2004012717 A1 | 2/2004 |
| WO | WO 2004/016248 A2 * | 2/2004 |
| WO | 2004035090 A1 | 4/2004 |
| WO | 2004/039357 A1 | 5/2004 |
| WO | 2004/058226 A1 | 7/2004 |
| WO | 2004103311 A2 | 12/2004 |
| WO | 2005/007139 A2 | 1/2005 |
| WO | 2005009381 A2 | 2/2005 |
| WO | 2005055955 A2 | 6/2005 |

OTHER PUBLICATIONS

Gardiner, K. R., et al., Abstract Only: Adsorbents as antiendotoxin agents in expeimental colitis, GUT, 1993, pp. 51-55, vol. 34, No. 1.
Abdelbary, G. et al., "The preparation of orally disintegrating tablets using the a hydrophilic waxy binder", "Int. Journal of Pharmaceutics", 2004, pp. 423-433, vol. 278.
Breitkrutz, J., "Leakage of enteric (Eudragit (R) L) coated dosage forms in simulated gastric juice in the presence of poly(ethylene . . .", 2000, pp. 79-88, vol. 67.
Cao, N. et al., "Activated Carbon Produced from Charcoal Obtained by Vacuum Pyrolysis of Softwood Bark Residues", "Energy and Fuels", 2001, pp. 1263-1269, vol. 15.
Kim, Y. et al., "Purification and characterization of an erythromycin esterase from an erythromycin-resistant *Pseudomonas* sp.", "FEMS Microbiology Letters", 2002, pp. 239-244, vol. 210.
Pal, K. et al., "Esterification of Carboxymethylcellulose with Acrylic Acid Targeted Drug Delivery System", "Trends Biomater. Artif. Organs.", 2005, pp. 12-14, vol. 19, No. 1.
Reshetnikov, V. , "Evaluation of the Adsorption Capacity of Enterosorbents and Related Medicinal Preparation", 2003, pp. 246-251, vol. 37, No. 5.
Torre, D., et al. , "Ciproflaxin and Activated Charcoal: Pharmacokinetic Data", Jul. 1989, pp. S1015-S1016, vol. 11.
Watts, P. et al., "Colonic Drug Delivery", "Drug Development and Industrial Pharmacy", 1997, pp. 893-913, vol. 23, No. 9.
Zhang, Y. et al., "Physical Properties and Compact Analysis of Commonly Used Direct Compression Binders", "AAPS PharmSciTech", 2003, pp. 1-11, vol. 4, No. 4.
Khalil, S. et al., "The In Vitro Adsorption of Some Antibiotics on Antacids", "Pharmazie", 1976, pp. 105-109, vol. 31.

(Continued)

*Primary Examiner* — Sean Aeder
(74) *Attorney, Agent, or Firm* — Hultquist, PLLC; David S. Bradin

(57) ABSTRACT

Orally administrable, site-specific (colonic), particulate delivery systems including adsorbents are disclosed. When delivered specifically to the colon, they can remove various substances present in, or as they reach, the colon. Methods of treatment using the delivery systems, and methods of preparing the delivery systems, are also disclosed. The particulate delivery systems are based on adsorbent matrices encapsulated into and/or onto particles, which selectively deliver the adsorbents to the colon. Representative drug delivery devices include pectin beads, which can optionally be crosslinked with metal ions such as zinc and/or calcium. The delivery system protects the adsorbent and prevents its adsorbing effect in the upper gastro-intestinal (GI) tract. When the particles are made from pectin, and the beads are administered to the colon, specific pectinolytic enzymes in the colon degrade the pectin, allowing the adsorbent to be released and to be fully active. Antibiotics, toxins, and other absorbable substances present in the colon will then be inactivated by adsorption into or onto the adsorbent.

26 Claims, 9 Drawing Sheets

OTHER PUBLICATIONS

Papioannou, D. et al., "The role of natural and synthethic zeolites as feed additives on the prevention and/or treatment of certain farm animal diseases", "Microporous and Mesoporous Materials", Jun. 28, 2005, pp. 161-170, vol. 84.

Ramu, J. et al., "Adsorption of Chloera and Heat-Labile *Escherichia coli* Entetrotoxins by Various Adsorbents: an In Vitro Study", "Journal of Food Protection", 1997, pp. 358-362, vol. 60, No. 4.

Singh, G. et al., "Adsorption Characterisitics of Norfloxacin to Pharmaceutical Additives", 1988, pp. 1845-1856, Publisher: Marcel Dekker Inc.

Wakerly, Z., et al., "Studies on Amidated Pectins as Potential Carriers in Colonic Drug Delivery", "J. Pharm. Pharmacol.", 1997, pp. 622-625, vol. 49.

* cited by examiner

COLONIC DELIVERY OF ADSORBENTS

RELATED APPLICATION

This application claims priority to U.S. Provisional Patent Application Ser. No. 60/682,074, filed May 18, 2005, entitled "Colonic Delivery of Adorbents".

FIELD OF THE INVENTION

This application is in the field of colonic delivery of therapeutic agents, and specifically deals with the specific delivery of adsorbent materials to the colon.

BACKGROUND OF THE INVENTION

Bacterial resistance to antibiotics emerged shortly after the beginning of antibiotics use and has raised continuously since, but the magnitude of the problem was somehow hidden until the early nineties because of the continuous discovery and release of new antibacterial agents. Nowadays, however, we face a major global public health crisis because the pharmaceutical industry is short of new antibacterial agents. Global use of those available is still increasing and, as a consequence, the incidence of resistant bacteria in humans is reaching an alarming level worldwide.

Although bacterial resistance can emerge by direct selection of resistant pathogens at the site of infection, the increased resistance of bacterial pathogens is in most instances a two step process, in which resistance occurs first in commensal flora and is followed by horizontal transfer of resistance to pathogenic species.

However hidden, increased resistance in commensal intestinal flora is a quasi constant secondary effect of all antibiotic uses. Researchers have shown that orogastric administration of beta-lactamases in mice reduced beta-lactamase associated alterations of the indigenous microflora and overgrowth of pathogens. Transposition of this principle to humans to reduce emergence of intestinal resistance during antibiotic treatments requires the specific delivery of antibiotic-hydrolyzing enzymes to the colon. An example of this approach is described in PCT WO 2004/016248, filed on Aug. 6, 2003, the contents of which are hereby incorporated by reference in their entirety. However, there are still a large number of antibiotics which induce bacterial resistance, but can not be removed by specific enzymes. Further, many bacteria produce toxins, which cause side effects such as diarrhea when the toxins reach the colon.

Adsorbents are known to adsorb a variety of organic chemicals, such as antibiotics. However, the administration of adsorbents is typically counter-indicated with prescription of antibiotics, because the adsorbents can adsorb and therefore inactivate a large quantity of these antibiotics before they can reach the blood flow [References 3-5].

It is therefore an object of the present invention to provide a system that targets inactivating agents to the colon, using site-specific particulate delivery systems, as well as methods of inactivating antibiotics and other active agents, and methods for adsorbing deleterious or dangerous products such as, but not limited to, toxins, chemicals, allergens etc. It is a further object of the present invention to provide such a system, where the system specifically releases its content into the colon, and does not interfere with the normal site of absorption of an antibiotic, i.e. the upper gastrointestinal ("GI") tract. The present invention provides such systems and methods.

SUMMARY OF THE INVENTION

The present invention is directed to orally administrable, site-specific (colonic), particulate delivery systems. When the systems are delivered specifically to the colon, they are able to remove various substances present in, or as they reach, the colon. The invention is also directed to methods of treatment using the delivery systems, and methods of preparing the delivery systems.

The particulate delivery systems are based on adsorbent matrices encapsulated into and/or onto particles, which selectively deliver the adsorbents to the colon. Representative drug delivery systems include pectin-based beads, where the pectin can optionally be crosslinked with metal ions such as zinc and/or calcium ions, and the crosslinked pectin beads can optionally be reticulated with a polycationic polymer such as polyethyleneimine, chitosan, or polylysine. In addition to, or in place of the pectin, other polymers, such as chitosan, alginates, xanthan, curdlan, guar gum and other polysaccharides (particularly ionically crosslinkable polysaccharides), and Eudragit® (polymethylmethacrylate polymers), can also be used to reticulate the particles.

The role of the particulate delivery system is to protect the adsorbent and to prevent its adsorbing effect in the upper gastro-intestinal (GI) tract. When the particles are made from pectin, and the beads reach the colon, specific pectinolytic enzymes degrade the pectin, allowing the adsorbent to be released and to be fully active. Antibiotics, chemicals, toxins, and other adsorbable substances present in the colon will then be inactivated by adsorption into or onto the adsorbent.

Because the site-specific particulate delivery systems specifically release the adsorbents in the colon, they do not interfere to a significant extent with the normal absorption kinetics of the antibiotic or any other active substance while in the upper GI tract or elsewhere in the human body.

In one embodiment, the adsorbents are used to adsorb residual antibiotics, such as but not restricted to beta-lactams, cyclines, quinolones, macrolides and aminoglycosides, when antibiotics are administered in conjunction with (i.e., before, during, or after administration of) the system. In this embodiment, the beads can optionally also include enzymes capable of inactivating the antibiotics. Examples of these enzymes include enzymes which inactivate beta-lactams, quinolones and/or macrolides, such as beta-lactamases. It is believed that the adsorbent can help bring the antibiotic into contact with the enzyme, further assisting with the removal of the antibiotic from the colon of the patient.

In another embodiment, the adsorbents are used to adsorb deleterious or dangerous products such as, but not limited to, toxins, chemicals, allergens and the like absorbed or produced by bacteria and/or fungi and which can produce serious adverse effects in the colon.

In yet another embodiment, the adsorbents are used to adsorb pharmaceutical agents which are administered systemically, and which result in beneficial effects when they interact with receptors outside of the colon, but result in adverse side effects, such as diarrhea and/or constipation, when they interact with receptors in the colon.

The adsorbent-containing particles can be prepared using methods known to those of skill in the art. In one embodiment, the particles are prepared by mixing the adsorbent in a pectin solution, crosslinking the pectin with a metal cation such as zinc or calcium to form pectin beads that encapsulate the adsorbent, and then optionally reticulating the crosslinked pectin beads with a solution of polyethyleneimine or any other suitable polycationic polymer. The resulting pectin beads can then be included in any suitable drug delivery device, such as a tablet or capsule.

BRIEF DESCRIPTION OF THE FIGURES

In FIG. 7, diamonds represent activated charcoal at a concentration of 10 mg/mL, triangles represent attapulgite at a concentration of 200 mg/mL, and squares represent kaolin at a concentration of 200 mg/mL. In FIG. 8, triangles represent activated charcoal at a concentration of 10 mg/mL, diamonds represent activated charcoal at a concentration of 5 mg/mL, and circles represent activated charcoal at a concentration of 1 mg/mL.

DETAILED DESCRIPTION OF THE INVENTION

Figure 1:
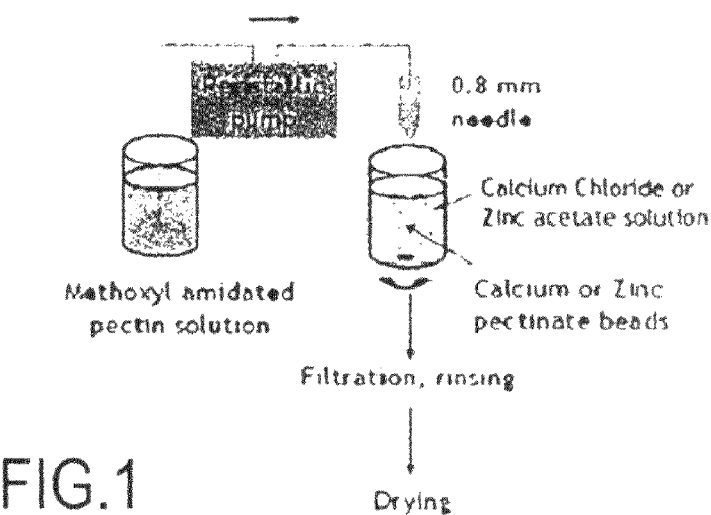
FIG. 1 represents a schematic view of a method that can be used to prepare the Zn-pectinate or Ca-pectinate beads described herein.

The particulate delivery systems including the encapsulated adsorbents, and methods of preparation and use thereof, are described in more detail below. As used herein, the terms "encapsulated" and "encapsulation" refers to adsorbents that are present in the beads and/or on the surface of the beads.

I. Components of the Adsorbent-Containing Particles

The adsorbent-containing particles include an adsorbent, and a polymeric component that does not release a significant amount of the adsorbent until the particles reach the colon.

A. Types of Adsorbents

The adsorbents used to prepare the particles must have a high specific surface, and can be of pharmaceutical grade or not. Examples of suitable adsorbents include activated charcoal, clays, including bentonite, kaolin, montmorrillonite, attapulgite, halloysite, laponite, and the like, silica, including colloidal silica (Ludox® AS-40 for example), mesoporous silica (MCM41), fumed silica, zeolithes and the like, talc, and resins for bacteriologic tests such as BACTEC® resins. Among these adsorbents, it can be preferred to use those of pharmaceutical grade, such as activated charcoal complying to Pharmacopoia standards (ex. Merck, France), kaolin (ex. VWR, France), attapulgite (ex. Lavollée, France), bentonite (ex. Acros Organics, France), Talc USP (ex. VWR, France).

B. Pectin Beads

Pectin is one example of a suitable polymer for preparing the particles, zinc and calcium ions are examples of suitable ions for ionically crosslinking the pectin in the particles (beads), and polyethyleneimine is an example of a suitable polymer for reticulating ionically-crosslinked pectin beads, in those embodiments where reticulation is desirable. Suitable pectin beads can be formed from pectin, a polyvalent (i.e., divalent or trivalent) metal ion, and optionally a cationic polymer, and the pectin beads can encapsulate one or more adsorbents.

Pectin

Pectin is a polysaccharide isolated from the cellular walls of superior vegetables, used widely in the agricultural food industry (as a coagulant or thickener of jams, ice creams and the like) and pharmaceutics. It is polymolecular and polydisperse. Its composition varies according to the source, extraction conditions and environmental factors.

Pectins are principally composed of linear chains of beta-1,4-(D)-galacturonic acids, at times interspersed by units of rhamnose. The carboxylic groups of galacturonic acids can be partially esterified to give methylated pectins. Two sorts of pectin are distinguished according to their degree of methylation (DM: number of methoxy group per 100 units of galacturonic acid):

highly methylated pectin (HM: high methoxy) whereof the degree of methylation varies between 50 and 80%. It is slightly soluble in water and forms gels in acidic medium (pH<3.6) or in the presence of sugars;

weakly methylated pectin (LM: low methoxy), with a degree of methylation varying from 25 to 50%. More soluble in water than pectin HM, it gives gels in the presence of divalent cations such as $Zn^{2+}$ and $Ca^{2+}$ ions. In effect, $Zn^{2+}$ and $Ca^{2+}$ ions form "bridges" between the carboxylated groups free of galacturonic acids. The network thus formed has been described by Grant et al. under the name of <<egg-box model>> (Grant G. T. et al. (1973) Biological interactions between polysaccharides and divalent cations: the egg-box model, *FEBS Letters*, 32, 195).

There are also amidated pectins. Using treatment of pectin by ammonia certain methyl carboxylate groups (—COOCH$_3$) can be transformed into carboxamide groups (—CONH$_2$). This amidation confers novel properties on the pectins, especially better resistance to variations in pH. Amidated pectins tend to be more tolerant to the variations in pH, and have also been studied for elaboration of matricial tablets for colonic deliver (Wakerly Z. et al. (1997) Studies on amidated pectins as potential carriers in colonic drug delivery, *Journal of Pharmacy and Pharmacology.* 49, 622).

Pectin is degraded by enzymes originating from higher vegetables and various microorganisms (i.e., fungi and bacteria) among which bacteria of human colonic flora is found. The enzymes produced by the microflora are composed of a set of polysaccharidases, glycosidases and esterases.

Other polymers, such as chitosan, alginates, xanthan, curdlan, guar gum and other polysaccharides (particularly ionically crosslinkable polysaccharides), and Eudragit® (polymethylmethacrylate polymers), can also be used to prepare the particles.

Metal Cations

In some embodiments, the pectin is ionically crosslinked with a metal cation. Any polyvalent (i.e., divalent, trivalent and the like) metal cation can be used to crosslink the pectin. Examples include calcium, zinc, aluminum, magnesium, iron, and the like. Zinc and calcium are preferred metal cations.

Cationic Polymer

In those embodiments where the pectin is ionically crosslinked with a metal cation, it can further optionally be reticulated with a cationic polymer, such as polyethyleneimine, chitosan or polylysine. It has been observed that when the pectin is crosslinked with zinc ions, such as those from zinc acetate, reticulation is less important than when calcium ions are used.

Of these cationic polymers, polyethyleneimine can be preferred. Polyethyleneimine is a strongly cationic polymer that binds to certain proteins, and is often used as a marker in immunology, to precipitate and purify enzymes and lipids. It is also known as aziridine polymer; epamine; epomine; ethylenimine polymer; montrek; PEI; and polymin(e). The molecular weight of the polyethyleneimine is between 10,000 and 100,000 Daltons, preferably between 20,000 and 50,000 Daltons.

The amount of polyethyleneimine used can be optimized, depending on the molecular weight and the type of pectin used. Advantageously, the optimal concentration for polyethyleneimine (when present at all) is that which provides reticulated pectin beads that are stable enough to survive in the gastrointestinal tract, yet unstable enough to be sufficiently degraded in the colon so as to release an effective amount of the adsorbent and/or the active agent. In some embodiments, such as where calcium ions are used to crosslink the pectin, it is believed that between 0 and 1% is the optimal range of concentrations of polyethyleneimine to achieve these goals.

For example, when the pectin beads are prepared from a pectin solution at 1-10% (w/v), advantageously from 2 to 6% (w/v), and a solution of calcium chloride at 2-10% (w/v), a concentration of 0 to 1% (w/v) of polyethyleneimine (PEI) is optimal.

Those of skill in the art, using the teachings described herein, can readily optimize the amount of polyethyleneimine, or avoid its use altogether, if there are variations in the concentration of pectin, the type of pectin, or the concentration or type of metal cation used, relative to that used in the working examples described herein. Further, in place of polyethyleneimine, other cationic polymers, such as chitosan or polylysine, can be used, provided they permit the pectin beads to specifically deliver the encapsulated adsorbent to the colon.

Disintegrating Agents

Disintegrating agents can be added to the pectin solution prior to ionotropic gelation. These disintegrating agents can hasten the disintegration of the beads in the colonic medium when needed. Representative disintegrating agents include D-lactose, polysorbate surfactants such as Tween® 80, poloxamers such as Lutrol® F68 (BASF), or polymers such as povidone Kollidon® K17, although other disintegrating agents known in the art can be used.

Optional Additional Components

The pectin beads can optionally include one or more additional components. Ideally, these are components that are not adsorbed by the adsorbent, and include excipients and enzymes which inactivate antibiotics or other adsorbed substances. For example, the enzymes can be enzymes which inactivate beta-lactams, quinolones and/or macrolides, such as beta-lactamases. While not wishing to be bound to a particular theory, it is believed that the adsorbent can help bring the antibiotic into contact with the enzyme, further assisting with the removal of the antibiotic from the colon of the patient.

II. Preparation of the Particulate Delivery Systems

The particles can be prepared by means known to those of skill in the art. When the particles are ionically-crosslinked pectin beads, they can typically be prepared by mixing the adsorbent and/or active agents in a pectin solution, crosslinking the pectin with a metal cation such as zinc or calcium to form pectin beads that encapsulate the adsorbent and/or active agents, and then optionally reticulating the beads with a solution of polyethyleneimine.

Typically, beads not containing the adsorbent are prepared by adding an aqueous pectin solution at a concentration of 1 to 10% (w/v) dropwise to a solution of a zinc salt such as zinc acetate, or a calcium salt such as calcium chloride, to form zinc or calcium pectinate beads, which are then recovered. Optionally, the ionically-crosslinked pectinate beads can be introduced to an aqueous solution of polyethyleneimine or other cationic polymer to reticulate the ionically crosslinked pectin beads.

A slightly different process is used to prepare beads including the adsorbents. The adsorbents are mixed with sufficient water to hydrate them and stirred for enough time to provide a homogenous suspension (typically 12 hours), and pectin (or a pectin solution) is added, with heating as necessary to maintain the viscosity of the solution. Then, the process proceeds in a substantially similar manner to that for preparing nude beads (i.e., beads that do not encapsulate an adsorbent).

The pectin solution is advantageously from 1 to 10% (w/v), preferably 2 to 6%, the zinc or calcium ion solution is advantageously from 2 to 15% (w/v), and the polyethyleneimine solution, when used, is advantageously from 0.5 to 2% (w/v). More preferably, the pectin solution is about 3% (w/v), the zinc solution is about 10% (w/v) or the calcium ion solution is about 6% (w/v), and the polyethylenimine solution, when used, is about 0,5 to 1% (w/v), preferably about 0.8% (w/v), although in any case, the amount of polyethyleneimine (if present at all) is advantageously selected to provide reticulated pectin beads that survive in the gastrointestinal tract until they reach the colon, and that are sufficiently degraded in the colon to provide effective release of the active agent.

The pectin beads are advantageously stirred in the zinc or calcium ion solution under slow agitation for between 10 minutes and 1 hour, preferably for about 20 to 30 minutes. About 200 beads are washed three times in 50 mL milli-Q water under slow agitation for between 0.5 and 10 minutes, preferably for about 1 minute. The number of washings can optionally be modified. The beads are optionally reticulated with polyethyleneimine under slow agitation for 15 to 40 minutes, preferably for 20 minutes and then washed according to the process describe above. After recovering the pectin beads, they are dried at a temperature of between 20 and 40° C. for 30 min to 10 hours, preferably at 37° C. for 2 hours or freeze-dried. The diameter of the particles is between about 0.5 mm and 5 mm, preferably between about 0.5 and 2 mm. The diameter of the particles can be finely tuned using different needle size and pectin flow through the needle.

In one embodiment, the pectin-based delivery systems are prepared according to the following process, which is based on the ionotropic gelation of pectin solution droplets when placed in a solution of a divalent or polyvalent metal ion such as zinc acetate or calcium chloride. The principle of the method is presented in FIG. 1.

In this embodiment, a pectin such as a methoxylated and amidated pectin (Unipectin OG175C, Degussa Texturant System, France) is dissolved into Milli-Q water using a magnetic stirrer. The solution can be heated around 50° C. to ease dissolution. The final pectin concentration is typically between 1% and 10% (w/v), although concentrations outside of this range can be used. The pectin solution is then driven with a peristaltic pump or a syringe pump through a needle (inner diameter: 0.5 mm) and falls drop by drop into a solution of a divalent or polyvalent metal ion, such as a zinc acetate or calcium chloride (with a typical salt concentration between about 1 and 12% w/v) at a typical rate of 60 to 80 beads a minute (although higher and lower rates can be used, and the rate may vary depending on the scale of the process).

To reduce its viscosity, the solution can be heated to around 50° C. or so while being pumped. The metal ions, such as zinc or calcium, interact with the $COO^-$ groups available on the pectin molecules according to the egg-box model [Reference 6]. Pectin drops are left to stir for 20 to 30 minutes or so in the salt bath to allow diffusion of the salt with the pectin matrix and full formation of the metal ion-pectinate (such as Zn-pectinate or Ca-pectinate) network. Beads are ideally then filtered, rinsed and washed at least three times with milli-Q water to eliminate the excess salt as described previously, and then dried. Drying can be achieved using any appropriate means, typically either by simply leaving the beads in the oven at around 37° C. for at least 2 hours, or by freeze-drying them.

Figure 2:
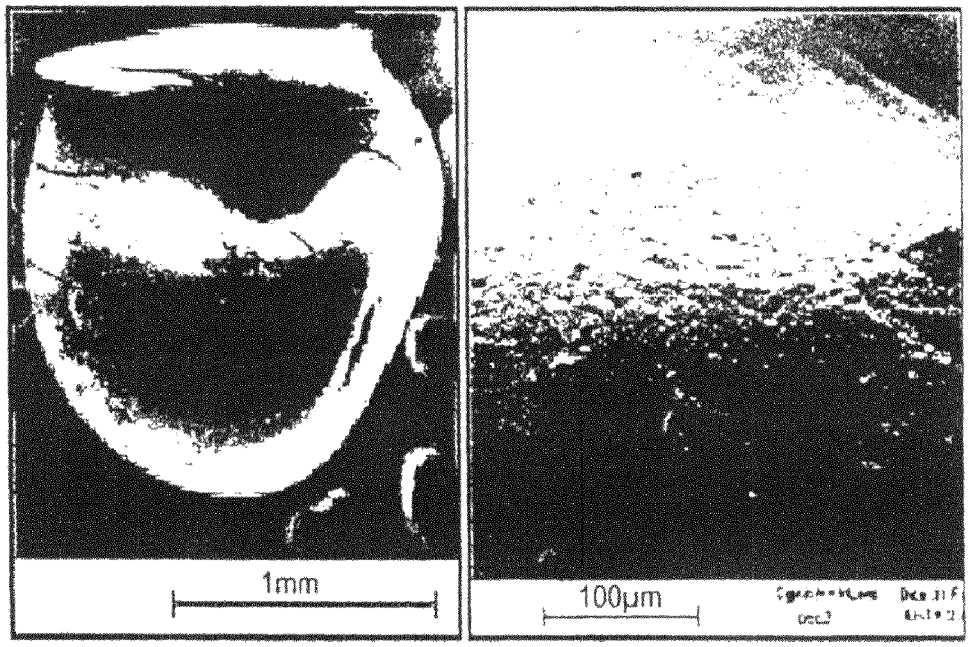
FIG. 2 shows Scanning Electron Microscopy (SEM) images of a typical Ca-pectinate dried bead (left) and its relatively smooth surface (right).
Figure 3:
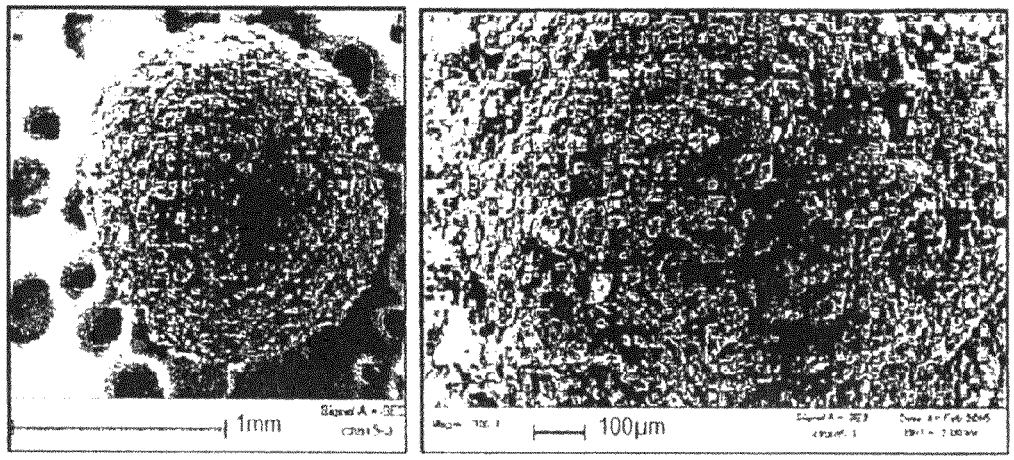
FIG. 3 shows calcium-pectinate beads encapsulating activated charcoal (charcoal to pectin ratio=5/3 w/w).
Figure 4:
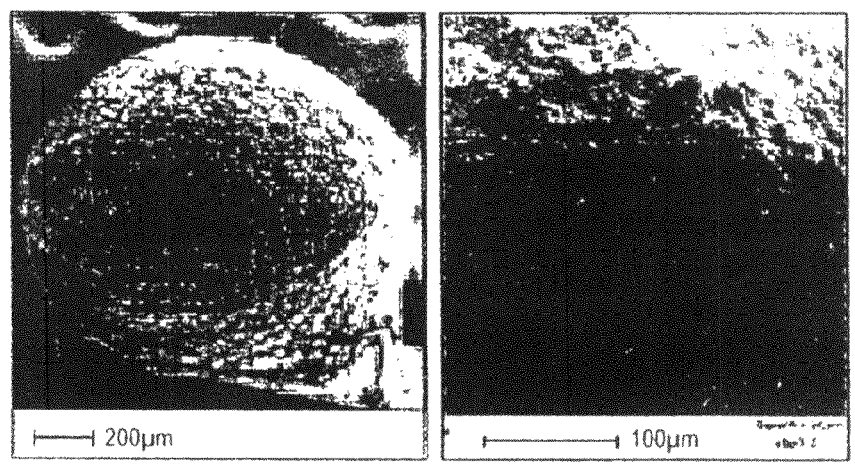
FIG. 4 shows calcium-pectinate beads encapsulating attapulgite (attapulgite to pectin ratio=1/1 w/w).
Figure 5:
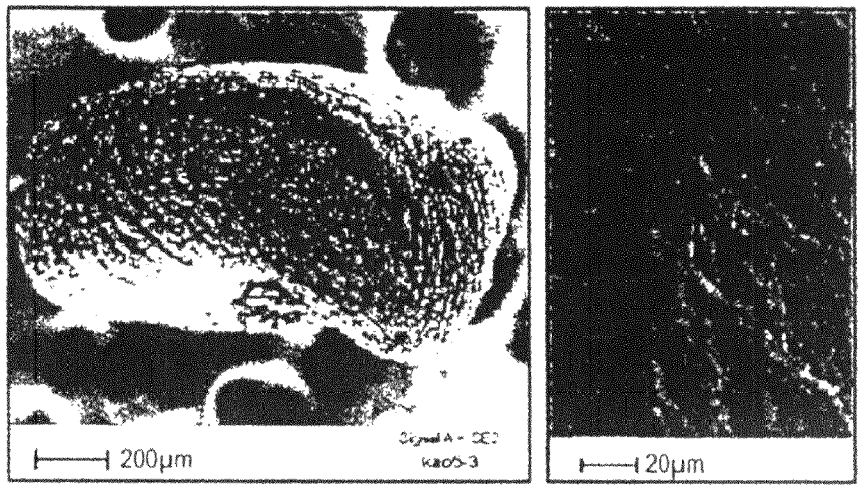
FIG. 5 shows calcium-pectinate beads encapsulating kaolin (kaolin to pectin ratio=5/3 w/w). On the right image the layered structure of kaolin is visible on the surface of the beads.
Figure 6:
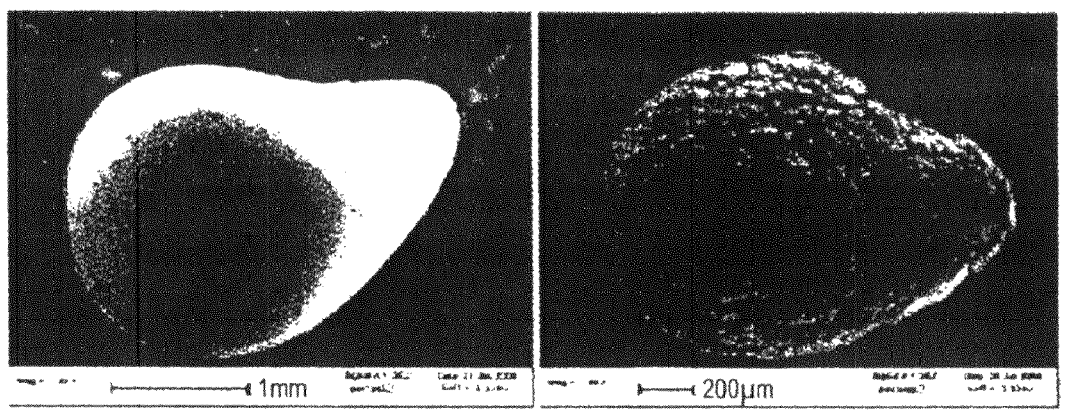
FIG. 6 shows SEM images of calcium pectinate beads encapsulating either colloidal silica (left, silica to pectin ratio=80/12 w/w) or laponite (right, laponite to pectin ratio=16/6 w/w).

After drying, nude-beads (i.e. not encapsulating anything) have a size around 1 millimeter. One can vary the size of the beads, for example, by varying the flow rate of the pectin solution, the size of the needle, the pectin concentration or the quantity of the encapsulated material. A typical dried nude bead is presented in FIG. 2. Nude beads have a rather smooth surface.

Encapsulation of the Adsorbents within Zn or Ca-Pectinate Beads

Encapsulation of the adsorbents was simply carried out by preparing separately a suspension of the adsorbent in water and a pectin solution. The adsorbent suspension was prepared as follows: the dry adsorbent was weighed and added to the water (concentration between 1 and 10% w/v) using a magnetic stirrer. The suspension was left to stir overnight to ensure that the adsorbent was fully hydrated (or exfoliated in the case of clays). This prolonged stirring seems to be also important for activated charcoal: if the adsorbent is not left to stir overnight, the suspension is not homogeneous and encapsulation is not easy. The pectin solution is heated (maximum 50° C.) and the adsorbent suspension was mixed with it using a three-blade propeller tool for at least 30 min. Mixing of the pectin solution with the adsorbent suspension is crucial for adequate and homogeneous encapsulation of the adsorbent within the pectin matrix. For example, if the adsorbent suspension is not left to stir overnight, a phase separation is observed when the pectin solution is added: a pectin rich phase and an adsorbent rich phase. The inhomogeneity disappears when the suspension is well hydrated overnight. In addition to pharmaceutical grade adsorbents, laponite XLG (Rockwood, UK) and colloidal silica (Ludox® AS-40, Sigma, France) were also encapsulated. Laponite was hydrated the same way as the natural clays. In the case of colloidal silica (40% w/v), since this adsorbent is already a suspension, it was mixed directly with the pectin solution using a three-blade propeller tool.

Adsorbent-containing beads can be prepared using the same method as described for nude beads. SEM images of dried beads are presented in FIGS. 3, 4, 5 and 6.

All beads have a rather rough surface in comparison with nude-beads. The roughness arises from the encapsulation of the adsorbents. Confirmation that encapsulation was homogeneous within the beads can be obtained by cutting the beads before drying and imaging the inside with scanning electron microscopy (not shown here). Adsorbents seem to be homogeneously distributed within the pectinate matrix. These results showed that despite formulation difficulties due to the high viscosity of pectin solutions, and the problems of phase separation, it is possible to incorporate important amounts of adsorbents within pectin solutions and then form Zn-pectinate or Ca-pectinate beads encapsulating a large quantity of these adsorbents.

The stability and adsorptive properties of beads prepared according to the methods described herein were evaluated in the Examples presented below.

III. Drug Delivery Systems including the Pectin Beads

The pectin beads can be collected, and combined with appropriate excipients and formulated into a variety of oral drug delivery devices. For example, the beads can be combined with a solid excipient, and tableted, or included in a capsule.

The pectin beads can also be combined with liquid/gel excipients which do not degrade the pectin beads, and the mixture/dispersion can be incorporated into a capsule, such as a gel-cap.

The tablets or capsules made with the pectin beads can be coated, if desired, with a suitable enteric coating to provide enhance stability while in the stomach without degradation. The pH in the stomach is of the order of 1 to 3 but it increases in the small intestine and the colon to attain values close to 7 (Hovgaard L. et al. (1996) Current Applications of Polysaccharides in Colon Targeting, *Critical Reviews in Therapeutic Drug Carrier Systems,* 13, 185). The drug delivery devices, in the form of tablets, gelatin capsules, spheroids and the like containing the pectin beads, can reach the colon, without being exposed to these variations in pH, by coating them with a pH-dependent polymer, insoluble to acidic pH but soluble in neutral or alkaline pH (Kinget et al. op. cit.). The polymers most current used for this purpose are derivatives of methacrylic acid, Eudragit® L and S (Ashford M. et al. (1993), An in vivo investigation into the suitability of pH-dependent polymers for colonic targeting, *International Journal of Pharmaceutics,* 95, 193 and 95, 241; and David A. et al. (1997) Acrylic polymers for colon-specific drug delivery, *S.T.P. Pharma Sciences,* 7, 546).

The drug delivery devices are administered in a chosen amount suitable to provide efficient treatment or prevention of the disorders for which the adsorbents are administered. Ideally, the effective dose of the adsorbents described herein is sufficient to provide the desired adsorptive effects in the colon, which may vary depending on the nature of the substance to be adsorbed.

Typically, the effective dose of the adsorbents is in an amount less than 100 mg/kg of body weight, often less than about 1 mg/kg patient weight and usually, but frequently, between about 10 mg to less than 100 mg/kg of patient weight. The foregoing effective doses typically represent that amount administered as a single dose, or as one or more doses administered over a 24-hour period.

IV. Methods of Treatment Using the Drug Delivery Devices Containing Adsorbent-Pectin Beads The drug delivery devices can be used to treat those types of conditions and disorders for which colonic delivery of adsorbents is appropriate. In one embodiment, the disorders are those that result from exposure of the colon to antibiotics, such as diarrhea. In this embodiment, the adsorbents inactivate antibiotics, and the devices can be administered in a therapeutically effective dosage to a patient who has been, is being, or will be given an antibiotic. Any antibiotic that can be adsorbed into/onto the adsorbent can be inactivated. Representative examples of antibiotics classes that can be adsorbed include beta-lactams, cyclines, macrolides, quinolones, aminoglycosides, glycopeptides, sulfamides, phenicols, sulfamides, furans, polypeptides, oxazolidones and antibiotics such as fosfomycin, rifampin and the like.

In another embodiment, the drug delivery devices can be administered to a patient who suffers from the effects of bacterial or fungal toxins present in the colon. Examples of such toxins include mycotoxins, endotoxins or enterotoxins, such as those produced by *Clostridium difficile* (believed to be a major cause of post-antibiotic diarrhea throughout the world). In this embodiment, the adsorbents are administered in a therapeutically effective dosage to adsorb the toxins.

In another embodiment, the drug delivery devices can be administered to a patient who suffers from a disorder treated with pharmaceutically active agents which bind to relevant receptors in the body of the patient other than in the colon to treat the disorder, but which, when bound to receptors in the colon, result in side effects. For example, the colon includes cholinergic (http://www.med-associates.com/gimm/gimmDrugScreen.htm) and serotonin receptors, which are also present in the central nervous system. Treatment with agents that bind to cholinergic receptors may result in side effects if the compounds bind to receptors in the colon. Co-administration of the adsorbent particles described herein and the agents that bind to such receptors can minimize or eliminate these side effects.

It is known that gastrointestinal problems are commonly reported adverse drug reactions with blood pressure medications (Calcium Channel blockers), pain medications (especially narcotics), antidepressants, antacids that contain aluminum and calcium, antiparkinson drugs, antispasmodics, diuretics, and anticonvulsants, and that many drug classes are associated with constipation. Often times, constipation persists, and patients discontinue treatment because the side effect is burdensome (http://www.med-associates.com/gimm/gimmDrugScreen.htm). Drugs such as risperidone can be associated with colonic disorders, such as megacolon (http://www.sma.org.sg/smj/4310/4310cr2.pdf).

The present invention will be further understood with reference to the following non-limiting examples.

Example 1

Stability of Loaded Beads in Simulated Gastro-Intestinal Media

The dissolution time of selected formulations, prepared using the methods described above, was evaluated in simulated gastric medium (SGM) (USP XXIV) (Table 1), simulated intestinal medium (SIM) (USP XXIV) (Table 2) and simulated colonic medium containing pectinolytic enzymes (SCM) (Table 3), under mild tangential stirring at 37° C.

TABLE 1

Disintegration time in the simulated gastic medium when calcium chloride (6% w/v) is replaced by zinc acetate (6% w/v) for ionotropic gelation. Beads were washed only once for this set of experiment.

| | Stability in SGM (pH = 1.2) Counter ion | |
|---|---|---|
| | Calcium chloride | Zinc acetate |
| Pectin (3% w/v) + Attapulgite (3% w/v) | No disintegration after 6 h | Not tested |
| Pectin (3% w/v) + Kaolin (5% w/v) | No disintegration after 6 h | Not tested |
| Pectin (3% w/v) + Activated charcoal (5% w/v) | Disintegration starts after 6 h | No disintegration after 6 h |

TABLE 2

Disintegration time in the simulated intestinal medium when calcium chloride (6% w/v) is replaced by zinc acetate (6% w/v) for ionotropic gelation. Beads were washed only once for this set of experiment.

| | Stability in SIM (pH = 6.8) Counter ion | |
|---|---|---|
| | Calcium chloride | Zinc acetate |
| Pectin (3% w/v) + Attapulgite (3% w/v) | Disintegration starts after 4 h | Not tested |
| Pectin (3% w/v) + Kaolin (5% w/v) | Disintegration starts after 2 h 30 | Not tested |

TABLE 2-continued

Disintegration time in the simulated intestinal medium when calcium chloride (6% w/v) is replaced by zinc acetate (6% w/v) for ionotropic gelation. Beads were washed only once for this set of experiment.

|  | Stability in SIM (pH = 6.8) Counter ion | |
| --- | --- | --- |
|  | Calcium chloride | Zinc acetate |
| Pectin (3% w/v) + Activated charcoal (5% w/v) | Disintegration starts after 2 h 30 | No disintegration after 6 h |

Enhancement of the stability in the simulated intestinal and colonic media is observed when calcium chloride is replaced by zinc acetate for ionotropic gelation.

TABLE 3

Stability of Zn-pectinate beads prepared with different concentrations of zinc acetate solution, in SIM and in SCM after 5 h in SIM. Beads washing process consisted in three rinsing of 1 minute in 50 mL Milli-Q water for about 200 beads.

| | Counter ion Zinc acetate (% w/v) | Stability in SIM (pH 6.8) | Stability in SCM (pH 6) with pectinolytic enzymes (5200 PG/mL) After 5 h in SIM |
| --- | --- | --- | --- |
| Pectin (3% w/v) + Activated charcoal (5% w/v) | 4 to 6 | Disintegration before 5 h | Not tested |
| | 8 10 12 | No disintegration after 5 h | Disintegration starts after 3 h |

The higher the zinc concentration used for ionotropic gelation, the more stable the beads in simulated intestinal medium (Table 3).

TABLE 4

Stability of Zn-pectinate beads prepared with different concentrations of zinc acetate, in SCM without pre-incubation in SIM. Beads washing process consisted in three rinsing of 1 minute in 50 mL Milli-Q water for about 200 beads.

| | Counter ion Zinc acetate (% w/v) | Stability in SCM (pH 6) with pectinolytic enzymes (5200 PG/mL) |
| --- | --- | --- |
| Pectin (3% w/v) + Activated charcoal (5% w/v) | 8 | Disintegration starts after 1 h Total disintegration after 3 h |
| | 10 | Disintegration starts after 1 h Total disintegration after 2 h 30 |
| | 12 | Disintegration starts after 1 h Total disintegration after 3 h |

Without pre-incubation in simulated intestinal medium, for zinc concentrations larger than 8% (w/v), the disintegration time in simulated colonic medium is comprised between 1 and 3 hours (Table 4).

TABLE 5

Stability of Zn—Ca-pectinate beads prepared with different concentrations of zinc acetate and calcium chloride mixtures, in SIM and in SCM after 5 h in SIM. Beads washing process consisted in three rinsing of 1 minute in 50 mL Milli-Q water for about 200 beads.

| | Counter ion mixture | | | Stability in SCM (pH 6) with pectinolytic enzymes (5200 PG/mL) After 5 h in SIM |
| --- | --- | --- | --- | --- |
| | Zinc acetate (% w/v) | Calcium chloride (% w/v) | Stability in SIM (pH 6.8) | |
| Pectin (3% w/v) + Activated charcoal (5% w/v) | 6 | 3 | No disintegration | Disintegration starts after 3 h |
| | | 6 | after 5 h | |
| | 12 | 3 | No disintegration | Disintegration starts after 3 h |
| | | 6 | after 5 h | |

Addition of calcium chloride to the 6% zinc acetate solution used for ionotropic gelation enhances the beads stability in SIM as compared with beads prepared without calcium (Table 5). However, no difference is observed when $CaCl_2$ is added to the 12% zinc acetate solution.

TABLE 6

Stability of Zn—Ca-pectinate beads prepared with different concentrations of zinc acetate and calcium chloride mixtures, in SCM without pre-incubation in SIM. Beads washing process consisted in three rinsing of 1 minute in 50 mL Milli-Q water for about 200 beads.

| | Counter ion mixture | | Stability in SCM (pH 6) with pectinolytic enzymes (5200 PG/mL) |
| --- | --- | --- | --- |
| | Zinc acetate (% w/v) | Calcium chloride (% w/v) | |
| Pectin (3% w/v) + Activated charcoal (5% w/v) | 6 | 3 | Disintegration starts after 1 h |
| | | 6 | Total disintegration after 2 h 30 |
| | 12 | 3 | Disintegration starts after 1 h |
| | | 6 | Total disintegration after 3 h |

Without pre-incubation in SIM, the beads stability in SCM is approximately the same for the different zinc and calcium concentrations that have been evaluated. The disintegration time in simulated colonic medium is comprised between 1 and 3 hours (Table 6).

TABLE 7

Stability of Ca-pectinate beads prepared with different concentrations of calcium chloride and coated with polyethylenemine, in SIM and in SCM after 5 h in SIM. Beads washing process consisted in three rinsing of 1 minute in 50 mL Milli-Q water for about 200 beads.

| | Counter ion Calcium chloride (% w/v) | Coating PEI (% w/v) | Stability in SIM (pH 6.8) | Stability in SCM (pH 6) with pectinolytic enzymes (5200 PG/mL) After 5 h in SIM |
| --- | --- | --- | --- | --- |
| Pectin (3% w/v) + Activated charcoal (5% w/v) | 2 | 0.6 0.8 1 | No disintegration after 5 h | Disintegration starts after 5 h |
| | 6 | 0.6 0.8 1 | No disintegration after 5 h | Disintegration starts after 5 h |

PEI coating considerably enhances beads stability in both the simulated intestinal medium and the simulated colonic medium as compared with uncoated Ca-pectinate beads (Table 7).

TABLE 8

Stability of Ca-pectinate beads prepared with different concentrations of calcium chloride and coated with polyethylenemine, in SCM without pre-incubation in SIM. Beads washing process consisted in three rinsing of 1 minute in 50 mL Milli-Q water for about 200 beads.

|  | Counter ion Calcium chloride (% w/v) | Coating PEI (% w/v) | Stability in SCM (pH 6) with pectinolytic enzymes (5200 PG/mL) |
|---|---|---|---|
| Pectin (3% w/v) + Activated charcoal (5% w/v) | 2 | 0.6 0.8 1 | Disintegration starts after 5 h |
|  | 6 | 0.6 0.8 1 | Disintegration starts after 5 h |

Without preincubation in SIM, PEI coating considerably enhances beads stability in the simulated colonic medium as compared with uncoated Ca-pectinate beads (Table 8).

TABLE 9

Stability of zinc-pectinate beads including a disintegrating agent, in SIM and in SCM after 5 h in SIM. Beads washing process consisted in three rinsing of 1 minute in 50 mL Milli-Q water for about 200 beads.

|  |  | Counter ion Zinc acetate (% w/v) | Stability in SIM (pH 6.8) | Stability in SCM (pH 6) with pectinolytic enzymes (5200 PG/mL) After 5 h in SIM |
|---|---|---|---|---|
| Pectin (3% w/v) + Activated charcoal (5% w/v) + disintegrating agent | d-lactose USP (% w/v) | 10 | 10 | No disintegration after 5 h | Disintegration starts after 3 h |
|  |  | 12 | 10 | No disintegration after 5 h | Disintegration starts after 3 h |
|  |  | 20 | 10 | No disintegration after 5 h | Disintegration starts after 3 h |
|  | PVP Kollidon® K17 PF (% w/v) | 0.5 | 10 | No disintegration after 5 h | Disintegration starts after 3 h |
|  |  | 1 |  | No disintegration after 5 h | Disintegration starts after 4 h |
|  |  | 5 |  |  |  |
|  |  | 10 |  |  |  |
|  | POE sorbitan monooleate Tween® 80 (% w/v) | 1 | 10 | No disintegration after 5 h | Disintegration starts after 3 h |
|  |  | 5 |  | No disintegration after 5 h | Disintegration starts after 1 h 30 Total disintegration after 3 h |
|  |  | 10 |  |  |  |
|  | Poloxamer 188 Lutrol® F68 (% w/v) | 0.1 | 10 | No disintegration after 5 h | Disintegration starts after 3 h |
|  |  | 0.5 |  |  |  |
|  |  | 1 |  | No disintegration after 5 h | Disintegration starts after 2 h Total disintegration after 3 h15 |
|  |  | 5 |  |  |  |
|  |  | 10 |  | No disintegration after 5 h | Disintegration starts after 2 h 30 Total disintegration after 4 h |

The different disintegrating agents tested do not influence the stability of the beads in the SIM: all the formulations are stable for at least 5 hours (Table 9). The inclusion of d-lactose or Kollidon® K17 does not modify the disintegration time of the beads in the SCM after incubation in the SIM, as compared with Zn-pectinate beads prepared without disintegrating agent. On the other hand, large concentrations of Tween® 80 (c=10% (w/v)) and medium concentrations of Lutrol® F68 (c=5% (w/v)) diminish the beads stability in the SCM after incubation in the SIM. For Tween® 80 (c=10% (w/v)), the disintegration starts after 1.5 hours of incubation in SCM and is over after 3 hours. For Lutrol® F68 (c=5% (w/v)), the disintegration starts after 2 hours of incubation in SCM and is over after 3 hours and 15 minutes.

TABLE 10

Stability of zinc-pectinate beads including a disintegrating agent, in SCM without pre-incubation in SIM. Beads washing process consisted in three rinsing of 1 minute in 50 mL Milli-Q water for about 200 beads.

|  |  | Counter ion Zinc acetate (% w/v) | Stability in SCM (pH 6) with pectinolytic enzymes (5200 PG/mL) |
|---|---|---|---|
| Pectin (3% w/v) + Activated charcoal (5% w/v) + disintegrating agent | d-lactose USP (% w/v) | 10 | 10 | Disintegration starts after 1 h Total disintegration after 2 h 30 |
|  |  | 12 | Disintegration starts after 1 h Total disintegration after 4 h |
|  |  | 20 | 10 | Disintegration starts after 1 h |

TABLE 10-continued

Stability of zinc-pectinate beads including a disintegrating agent, in SCM without pre-incubation in SIM. Beads washing process consisted in three rinsing of 1 minute in 50 mL Milli-Q water for about 200 beads.

|  |  | Counter ion Zinc acetate (% w/v) | Stability in SCM (pH 6) with pectinolytic enzymes (5200 PG/mL) |
|---|---|---|---|
|  |  |  |  | Total disintegration after 3 h |
|  | PVP Kollidon® K17 | 0.5 | 10 | Not tested |
|  |  | 1 |  | Disintegration starts after 45 min |

TABLE 10-continued

Stability of zinc-pectinate beads including a disintegrating agent, in SCM without pre-incubation in SIM. Beads washing process consisted in three rinsing of 1 minute in 50 mL Milli-Q water for about 200 beads.

|  | Counter ion Zinc acetate (% w/v) | Stability in SCM (pH 6) with pectinolytic enzymes (5200 PG/mL) |
|---|---|---|
| PF (% w/v) | 5 | Total disintegration after 1 h 15 |
|  | 10 |  |
| POE sorbitan monooleate Tween ® 80 (% w/v) | 1 | 10 Disintegration starts after 2 h Total disintegration after 3 h 30 |
|  | 5 | Disintegration starts after 30 min Total disintegration after 1 h 15 |
|  | 10 |  |
| Poloxamer 188 Lutrol ® F68 (% w/v) | 0.1 | 10 Disintegration starts after 1 h Total disintegration after 1 h 30 |
|  | 0.5 | Disintegration starts after 1 h Total disintegration after 1 h 30 |
|  | 1 | Disintegration starts after 30 min Total disintegration after 1 h 30 |
|  | 5 | Disintegration starts after 30 min Total disintegration after 1 h 15 |
|  | 10 | Disintegration starts after 2 h 30 Total disintegration after 4 h |

As already observed with preincubation in SIM, two formulations are of interest when one needs fast disintegration: Tween® 80 (c=10% (w/v)) and Lutrol® F68 (c=5% (w/v)) (Table 10).

Example 2

Adsorption Efficiency in Simulated Colonic Conditions with Bare Adsorbents

Adsorption of three pharmaceutical grade adsorbents was tested for amoxicillin and ciprofloxacin under simulated colonic conditions by determining residual concentration of antibiotics, using HPLC. The simulated colonic medium (SCM) used for these experiments was the following: HEPES (2.383 g/L) and NaCl (8.474 g/L) solution (pH 6). Adsorbents were incubated in the colonic medium described above at 37° C. under gentle tangential stirring. At desired time points, suspensions were collected and centrifuged at 10,000 RPM using a micro-centrifuge. The supernatant was filtered on a syringe driven filter unit (Millex®-HV, 0.45 µm, PVDF, 4 mm; Millipore, France) and assayed for their antibiotic concentration using HPLC. Control samples of the tested SCM were incubated with the same experimental conditions. The percentage of antibiotics remaining in the SCM after incubation with adsorbents was determined by comparison with incubated controls.

Adsorption Kinetics of Amoxicillin

The capacity of attapulgite, activated charcoal and kaolin to adsorb amoxicillin in simulated colonic conditions was studied. The concentration of amoxicillin before and after exposure to the adsorbents was determined using HPLC coupled with UV detection ($\lambda$=230 nm). The separation was achieved using Ypersphere® 5 µm (250×4.6 mm, Interchim, France), a C18 reversed-phase column, at room temperature. The mobile phase consisted of a 95% phosphate solution ($KH_2PO_4$, 0.01 M, acidified at pH 3 with orthophosphoric acid) and 5% acetonitrile mixture. The flow rate was fixed at 1.3 mL/min. Experimental conditions and results of binding experiments with amoxicillin are shown in Table 11.

TABLE 11

Experimental conditions and characteristics of the amoxicillin elimination by adsorption onto bare adsorbents.

|  | [Amoxicillin] (mg/mL) | Incubation time (min) | Adsorption | Plateau (min) | Eliminated Amox. (%) |
|---|---|---|---|---|---|
| [Attapulgite] (mg/mL) |  |  |  |  |  |
| 0.5 | 2 | 0, 30, 60, 180 | – |  |  |
| 5 | 2 | 0, 30, 60, 180 | – |  |  |
| 20 | 1 | 0, 30, 60, 180 | – |  |  |
| *200 | 0.5 | 0, 30, 60, 120, 180, 360 | + | >360 | ≈45 |
| 200 | 1 | 0, 180, 900 | + | >360 | ≈25 |
| [Kaolin] (mg/mL) |  |  |  |  |  |
| 0.5 | 2 | 0, 30, 60, 180 | – |  |  |
| 5 | 2 | 0, 30, 60, 180 | – |  |  |
| 20 | 1 | 0, 30, 60, 180 | – |  |  |
| *200 | 0.5 | 0, 30, 60, 120, 180, 360 | + | >360 | ≈25 |
| 200 | 1 | 0, 180, 900 | + | >180 | ≈30 |

TABLE 11-continued

Experimental conditions and characteristics of the amoxicillin elimination by adsorption onto bare adsorbents.

| | [Amoxicillin] (mg/mL) | Incubation time (min) | Adsorption | Plateau (min) | Eliminated Amox. (%) |
|---|---|---|---|---|---|
| [Activated charcoal] (mg/mL) | | | | | |
| **1 | 1 | 0, 5, 15, 30, 60, 120, 180, 360 | + | 15-30 | ≈25 |
| **5 | 1 | 0, 5, 15, 30, 45, 60 | ++ | 15 | 75 |
| *10 | 0.5 | 0, 5, 15, 30, 60, 120, 180, 360 | ++ | 15 | >95 |
| ** | 1 | 0, 5, 15, 30, 45, 60 | ++ | 15 | >95 |

*FIG. 7.
**FIG. 8.

Figure 7:
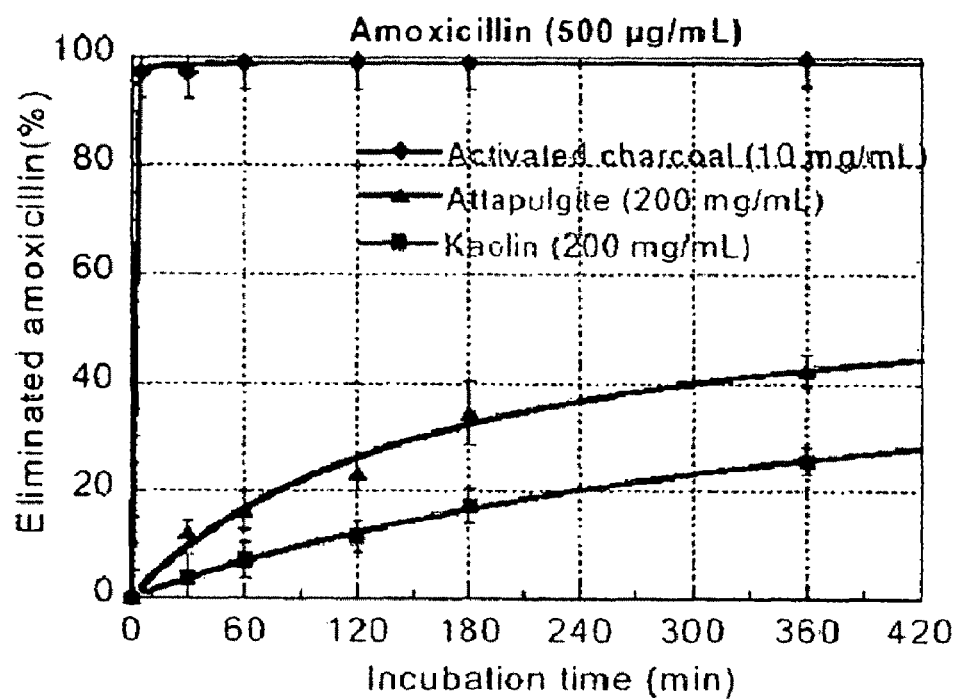
FIGS. 7 and 8 present the percentage of amoxicillin eliminated by adsorption (%) (0.5 and 1 mg/mL) versus contact time (min.) of incubation with each adsorbent tested, in Simulated Colonic Medium (SCM) without pectinolytic enzymes.
Figure 8:
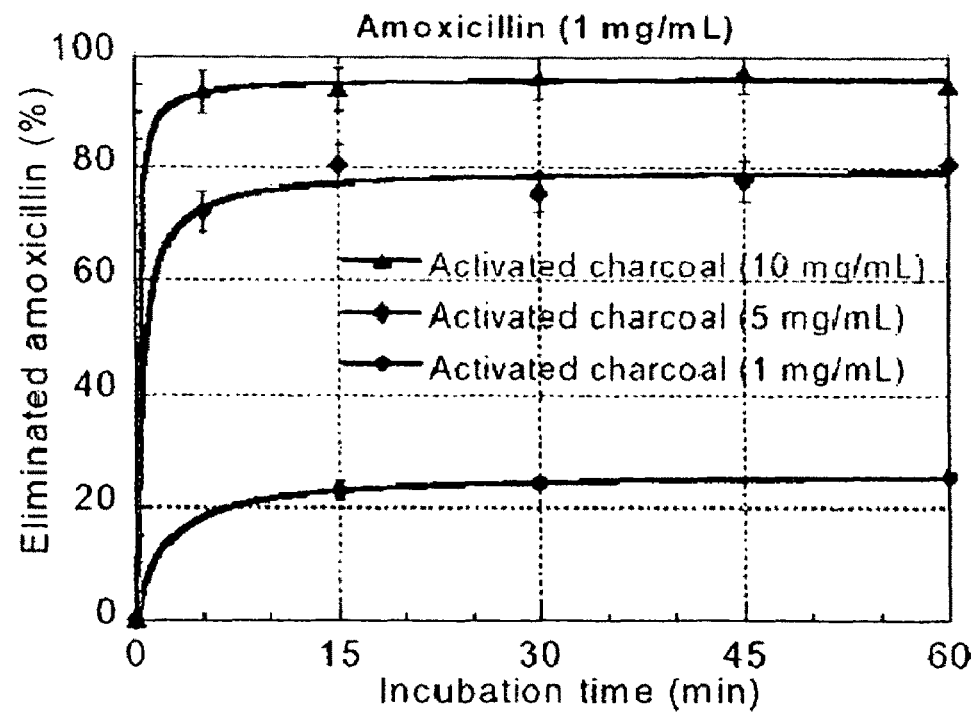

FIGS. 7 and 8 present the percentage of eliminated amoxicillin (0.5 and 1 mg/mL) versus contact time with each adsorbent tested, in SCM without pectinolytic enzymes. As shown in these figures, amoxicillin adsorption is very efficient with activated charcoal whereas it is observed at a lesser degree with attapulgite and kaolin. After 6 hours of incubation, the percentage of eliminated amoxicillin from the different adsorbents varied from around 25% to up to 95% with greater reduction for activated charcoal. These results display that the maximum of adsorption is always reached after a relatively short contact time with activated charcoal. The plateau appears after 15 to 30 min of incubation regardless of the concentration of amoxicillin tested (0.5 and 1 mg/mL) and the amount of charcoal (1, 5 and 10 mg/mL). Attapulgite and kaolin do reduce amoxicillin concentration, but for higher concentration (200 mg/mL) and the steady state is reached only after 6 hours.

Furthermore, results presented in FIG. 8 demonstrate that the adsorption velocity is not related to the charcoal concentration. However, the amount of amoxicillin adsorbed at saturation is strongly dose dependent.

Results obtained for activated charcoal were very promising. They evidence that rather small quantities of this adsorbent (1 mg/mL to 10 mg/mL) enabled one to eliminate amoxicillin at a concentration comprised between 0.250 mg/mL and 1 mg/mL of feces. From what is known about amoxicillin pharmacology, the expected residual concentration of amoxicillin in feces (around 5 to 10% of standard oral doses (1 to 2 g/day)) which corresponds to 0.08 to 0.33 mg/mL of feces. This concentration range is in agreement with the concentration range that the particles described herein are able to inactivate.

Adsorption Kinetics of Ciprofloxacin

Ciprofloxacin concentration after contact with bare adsorbents was determined using HPLC coupled with UV detection at 278 nm. Control samples were prepared like mentioned above. The separation was achieved at 25° C., using a C18 Symmetry® column (5 μm, 150×4.6 mm; Waters, France). The mobile phase was 10% acetonitrile in 0.02 M $NaH_2PO_4$ solution (acidified at pH 3 with orthophosphoric acid). The flow rate was 1 mL/min.

Table 12 presents the experimental conditions and the results of adsorption kinetics with ciprofloxacin.

TABLE 12

Experimental conditions and characteristics of the ciprofloxacin elimination by adsorption onto bare adsorbents.

| | [Ciprofloxacin] (μg/mL) | Incubation time (min) | Adsorption | Plateau (min) | Eliminated Cipro. (%) |
|---|---|---|---|---|---|
| [Attapulgite] (mg/mL) | | | | | |
| *1 | 100 | 0, 15, 60, 180 | + | 15-30 | ≈45 |
| [Kaolin] (mg/mL) | | | | | |
| *1 | 100 | 0, 15, 60, 180 | + | 15 | ≈10 |
| 10 | 100 | 0, 15, 60, 180 | ++ | 15-30 | ≈80 |
| [Activated charcoal] (mg/mL) | | | | | |
| *1 | 100 | 0, 15, 60, 180 | ++ | 15 | >95 |
| **1 | 500 | 0, 15, 60, 180 | + | 15-30 | ≈45 |

*FIG. 9.
**FIG. 10.

Figure 9:
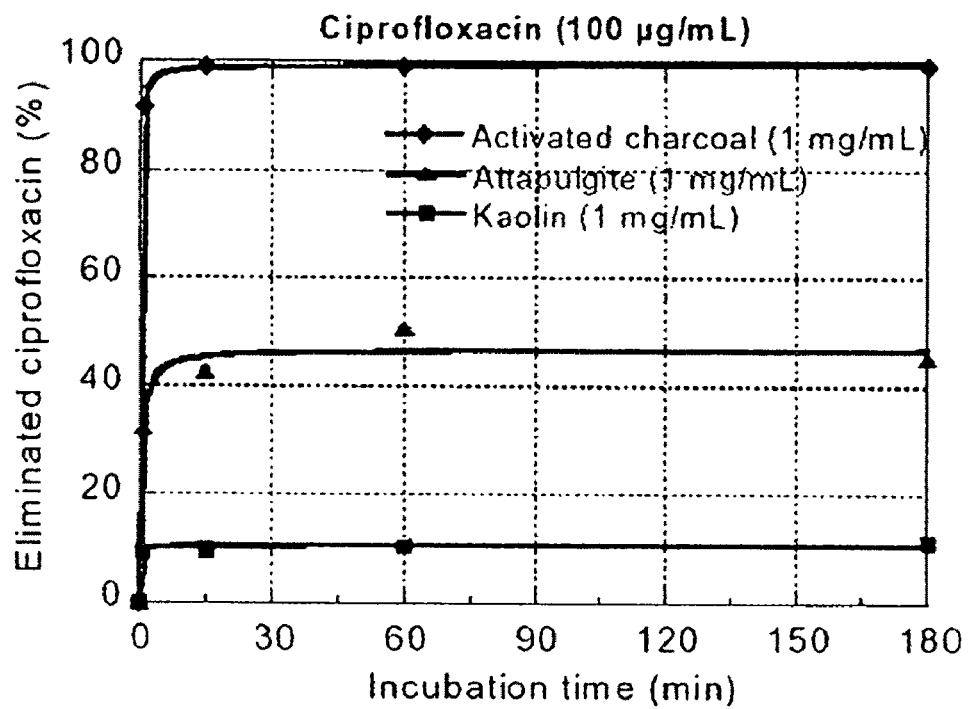
FIG. 9 represents the percentage of ciprofloxacin eliminated by adsorption (%) (initial concentration is 100 µg/mL) versus time (min) of incubation with adsorbent matrices in SCM without pectinolitic activity. Triangles represent activated charcoal at a concentration of 1 mg/mL, diamonds represent attapulgite at a concentration of 1 mg/mL, and squares represent kaolin at a concentration of 1 mg/mL.
Figure 10:
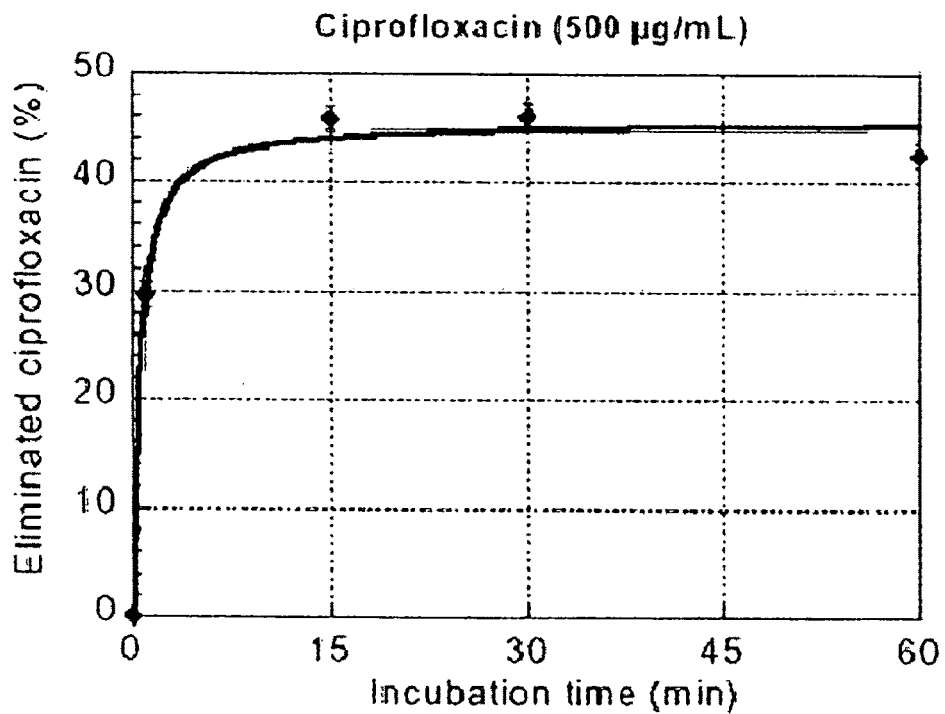
FIG. 10 represents the percentage of ciprofloxacin eliminated by adsorption (%) (initial concentration is 500 µg/mL) versus time (min) of incubation with adsorbent matrices including activated charcoal at a concentration of 1 mg/mL in SCM without pectinolitic activity.

FIG. 9 presents the percentage of eliminated ciprofloxacin eliminated by adsorption versus time of incubation with adsorbent matrices. In comparison with amoxicillin, it was observed that the velocity of adsorption is faster for the three adsorbents tested. The plateau is reached between 15 and 30 minutes independently of the adsorbent used. As already seen with amoxicillin, activated charcoal exhibits higher adsorption capacity than attapulgite, which is more efficient than kaolin. As shown in FIG. 10, when ciprofloxacin concentration is increased five fold, the adsorption equilibrium onto charcoal still happens after 15 to 30 min of incubation. Moreover, activated charcoal at 1 mg/mL was still efficient in eliminating the antibiotic by adsorption (45% of 0.5 mg/mL), which was eliminated in 15 to 30 minutes. Even though only 45% of the initial concentration was inactivated, it still represented quantitatively a higher amount of antibiotic eliminated by adsorption: around 0.225 mg/mL. These results are in agreement with expected residual concentration of ciprofloxacin in feces, which means a maximum of 25% of oral doses (1 to 1.5 g/day), i.e. around 0.420 mg/mL to 0.625 mg/mL.

Example 3

Adsorption Efficiency in Simulated Colonic Conditions with Encapsulated Adsorbents Experiment 1: Ca-pectinate beads encapsulating activated charcoal were used for this experiment. The activated charcoal to pectin ratio was 5/3 (w/w). Beads were washed only once for this experiment. The efficiency of the adsorbent to reduce ciprofloxacin concentration after release from the pectin was determined under simulated colonic conditions. The SCM used for this study was the following: HEPES (2.383 g/L) and NaCl (8.474 g/L) solution (pH 6) containing a pectinolytic enzyme solution (Pectinex® SPL Ultra, Sigma, France) (1/20; v/v).

Beads were incubated in the SCM described above containing ciprofloxacin at 37° C. under gentle tangential stirring. At desired time points samples were centrifuged at 10,000 RPM using a microcentrifuge. The supernatant was filtered on syringe driven filter unit (Millex®-HV, 0.45 μm, PVDF, 4 mm) and analyzed using HPLC.

Adsorption Kinetics of Ciprofloxacin

Table 13 presents experimental conditions and percentages of ciprofloxacin eliminated by adsorption from activated charcoal after its release from Ca-pectinate beads.

Figure 11A:
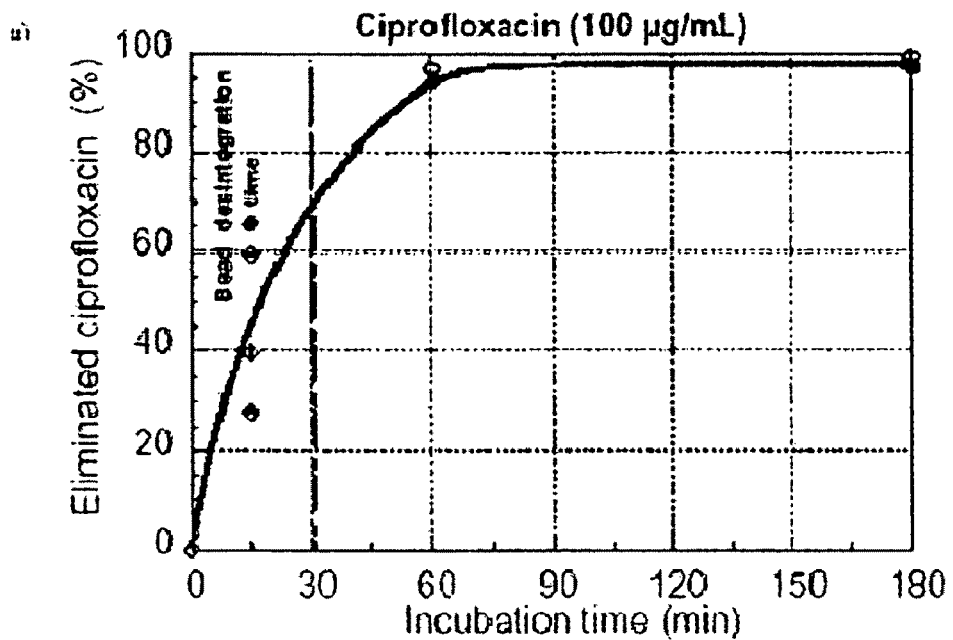
FIG. 11a represents the percentage of ciprofloxacin eliminated by adsorption (%) (initial concentration is 100 µg/mL) versus time (min) of incubation with calcium pectinate beads loaded with activated charcoal (1 bead/mL) in simulated colonic medium containing pectinolytic enzymes.
Figure 11B:
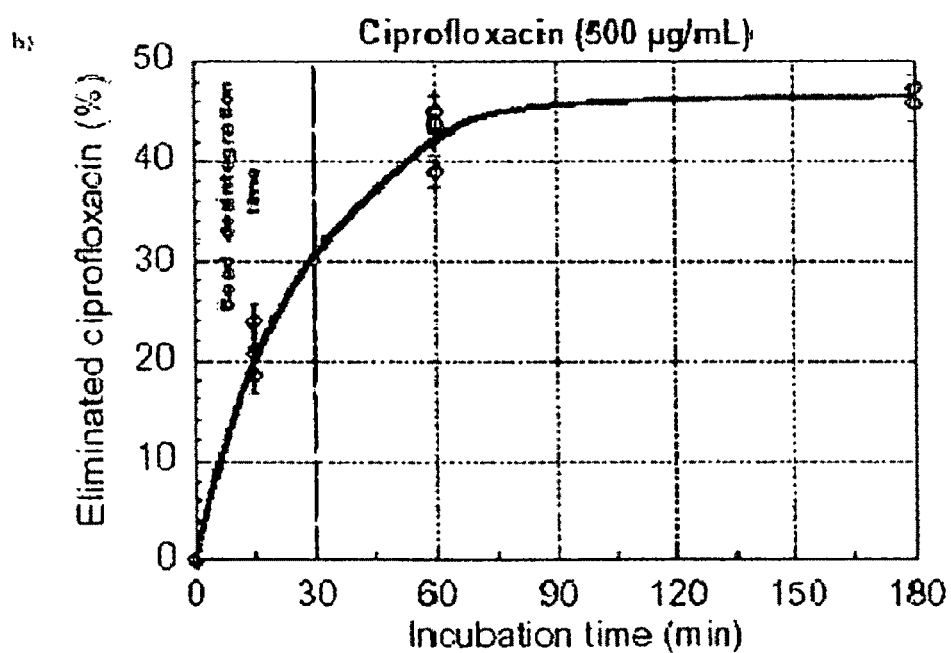
FIG. 11b represents the percentage of ciprofloxacin eliminated by adsorption (%) (initial concentration is 500 µg/mL) versus time (min) of incubation with calcium pectinate beads loaded with activated charcoal (1 bead/mL) in simulated colonic medium containing pectinolytic enzymes.

Using a SCM containing pectinases at 1/20, Ca-pectinate beads disintegrated completely after around 30 minutes. FIGS. 11a and b show that the ciprofloxacin was eliminated by adsorption when incubated with charcoal-loaded beads in SCM. Steady state was delayed in comparison with binding experiments with bare adsorbents. The differences observed in adsorption velocity might result from the time it takes for the Ca-pectinate matrix to disintegrate. At adsorption equilibrium, the amount of ciprofloxacin eliminated by adsorption was quantitatively the same as the amount adsorbed onto the non-encapsulated charcoal. This means that activated charcoal was indeed released from the beads when incubated in SCM containing pectinases and that its adsorption capacity was not affected by encapsulation.

Experiment 2: Ca-pectinate and Zn-pectinate beads encapsulating activated charcoal were used for this experiment. The activated charcoal to pectin ratio was 5/3 (w/w). Calcium concentration used for ionotropic gelation was 6% (w/v) and Zinc concentration used for ionotropic gelation was 6% (w/v). A gentle washing was performed; beads were washed only once for this experiment. The efficiency of the adsorbent to reduce ciprofloxacin concentration after release from the pectin was determined under simulated colonic conditions. The SCM used for this study was the following: HEPES (2.383 g/L) and NaCl (8.474 g/L) solution (pH 6) containing a pectinolytic enzyme solution (Pectinex® SPL Ultra, Sigma, France) (1/20; v/v).

Beads were incubated in the SCM described above containing ciprofloxacin at 37° C. under gentle tangential stirring. At desired time points samples were centrifuged at 10,000 RPM using a microcentrifuge. The supernatant was filtered on syringe driven filter unit (Millex®-HV, 0.45 μm, PVDF, 4 mm) and analyzed using HPLC. Typically, one bead was incubated with 1.5 mL SCM.

Figure 12:
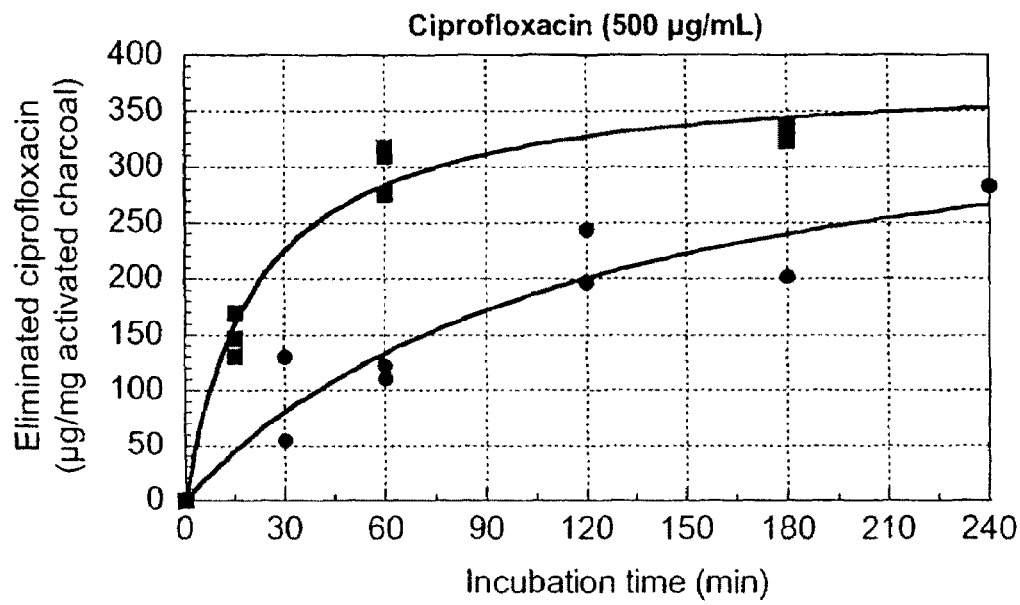
FIG. 12 represents the dose of ciprofloxacin eliminated by adsorption given in µg/mg activated charcoal versus time (min) of incubation; comparison between calcium-pectinate (blue squares) and zinc-pectinate (red circles) beads loaded with activated charcoal (6% w/v of counter ions). Beads are incubated in simulated colonic medium containing 500 µg/mL of ciprofloxacin (n=2).

FIG. 12 shows that both type of beads (Ca and Zn) are able to adsorb ciprofloxacin. The adsorption kinetics is longer for Zn-pectinate beads, probably due to their slower disintegration time in the SCM. Adsorption capacity of activated charcoal released from Ca-pectinate beads tends to reach the saturation after 3 hours of incubation while elimination of ciprofloxacin by adsorption onto activated charcoal released from Zn-pectinate beads still increases after 4 hours of contact.

Figure 13:
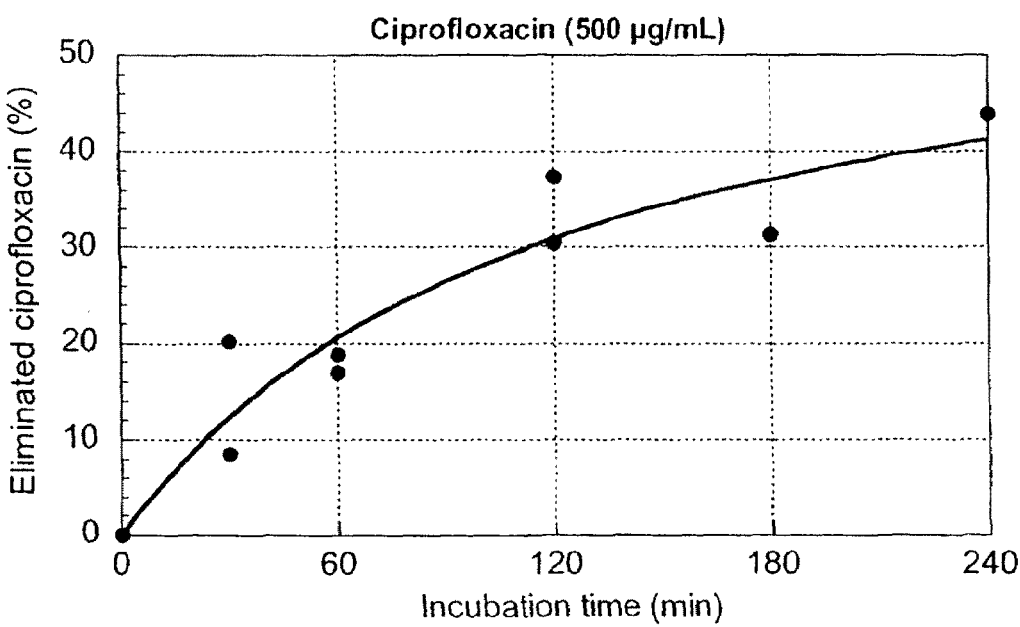
FIG. 13 represents the percentage of ciprofloxacin eliminated by adsorption versus time (min) of incubation with zinc pectinate beads loaded with activated charcoal (6% w/v of zinc acetate) in simulated colonic medium. The initial ciprofloxacin concentration is 500 µg/mL.

As shown in FIG. 13, about 40% of the initial ciprofloxacin is eliminated by adsorption after 4 hours of incubation in the SCM.

TABLE 13

Experimental conditions of the binding experiments and parameters of ciprofloxacin elimination by adsorption onto activated charcoal released from Ca-pectinate beads, under simulated colonic conditions.

| Ca-pectinate bead loaded with activated charcoal | [Ciprofloxacin] (μg/mL) | Incubation time (min) | Adsorption | Plateau (min) | Eliminated Ciprofloxacin (%) |
|---|---|---|---|---|---|
| 1 bead/mL | 100 | 0, 15, 60, 180 | ++ | 60-90 | >95 |
|  | 100 | 0, 15, 60, 180 | ++ | 60-90 |  |
|  | 100 | 0, 15, 60, 180 | ++ | 60-90 |  |
|  | 100 | 0, 15 | + |  | 59 |
|  | 500 | 0, 15, 60 | + | >60 | ≈40 |
|  | 500 | 0, 15, 60, 180 | + | 60-90 | ≈45 |
|  | 500 | 0, 15, 60, 180 | + | 60-90 | ≈45 |

Experiment 3: Zn-pectinate beads encapsulating activated charcoal were used for this experiment. The activated charcoal to pectin ratio was 5/3 (w/w). Zinc concentration used for ionotropic gelation was 10% (w/v). For this experiment, beads were washed three times for 1 minute. The efficiency of the adsorbent to reduce ciprofloxacin concentration after release from the pectin was determined under simulated colonic conditions. The SCM used for this study was the following: HEPES (2.383 g/L) and NaCl (8.474 g/L) solution (pH 6) containing a pectinolytic enzyme solution (Pectinex® SPL Ultra, Sigma, France) (1/5; v/v). Typically, one or two beads were incubated with SCM containing 100 µg/mL of ciprofloxacin (2 mg or 5 mg of beads/mL of SCM).

Beads were incubated in the SCM described above containing ciprofloxacin at 37° C. under gentle tangential stirring. At desired time points samples were centrifuged at 10,000 RPM using a microcentrifuge. The supernatant was filtered on syringe driven filter unit (Millex®-HV, 0.45 µm, PVDF, 4 mm) and analyzed using HPLC.

Figure 14:
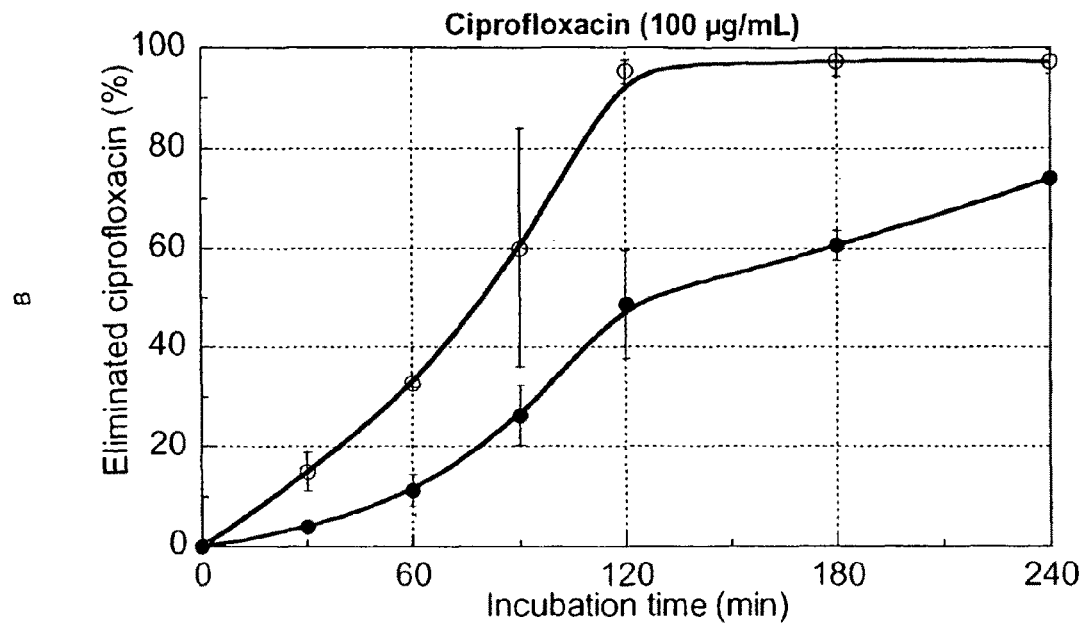
FIG. 14 represents the percentage of ciprofloxacin eliminated by adsorption versus time (min) of incubation with zinc-pectinate beads with activated charcoal (10% w/v of zinc acetate) in the simulated colonic medium. Beads (2 mg/mL (blue filled circles) or 5 mg/mL (blacknempty circles)) are incubated in simulated colonic medium containing an initial ciprofloxacin concentration of 100 µg/mL.

As shown in FIG. 14, adsorption kinetics of ciprofloxacin by activated charcoal loaded Zn-pectinate beads is a two step process. Before the beads are fully disintegrated, ciprofloxacin is adsorbed slowly and weakly (only around 10% or 30% adsorbed during the first hour of incubation, for 2 mg or 5 mg beads/mL SCM respectively). After an hour of incubation, beads have released their charcoal content and the adsorption is faster and stronger. After 4 hours of incubation up to 70% of the initial ciprofloxacin is eliminated by a charcoal concentration of 2 mg/mL SCM. An increase of the bead amount to 5 mg/mL SCM leads to an increase of the adsorption velocity onto the matrix; adsorption process tends to a plateau after 2 hours of incubation and after 4 hours up to 95% of the initial ciprofloxacin is removed by adsorption.

Experiment 4: Zn-pectinate beads encapsulating activated charcoal were used for this experiment. The activated charcoal to pectin ratio was 5/3 (w/w). Zinc concentration used for ionotropic gelation was 10% (w/v). Beads were formulated with 10% (w/v) Tween 80. Beads were washed three times for 1 minute. The efficiency of the adsorbent to reduce ciprofloxacin concentration after release from the pectin was determined under simulated colonic conditions. The SCM used for this study was the following: HEPES (2.383 g/L) and NaCl (8.474 g/L) solution (pH 6) containing a pectinolytic enzyme solution (Pectinex® SPL Ultra, Sigma, France) (1/5; v/v). Typically, one bead was incubated with SCM containing 100 µg/mL of ciprofloxacin (2 mg of beads/1 mL of SCM).

Beads were incubated in the SCM described above containing ciprofloxacin at 37° C. under gentle tangential stirring. At desired time points samples were centrifuged at 10,000 RPM using a microcentrifuge. The supernatant was filtered on syringe driven filter unit (Millex®-HV, 0.45 µm, PVDF, 4 mm) and analyzed using HPLC.

Figure 15:
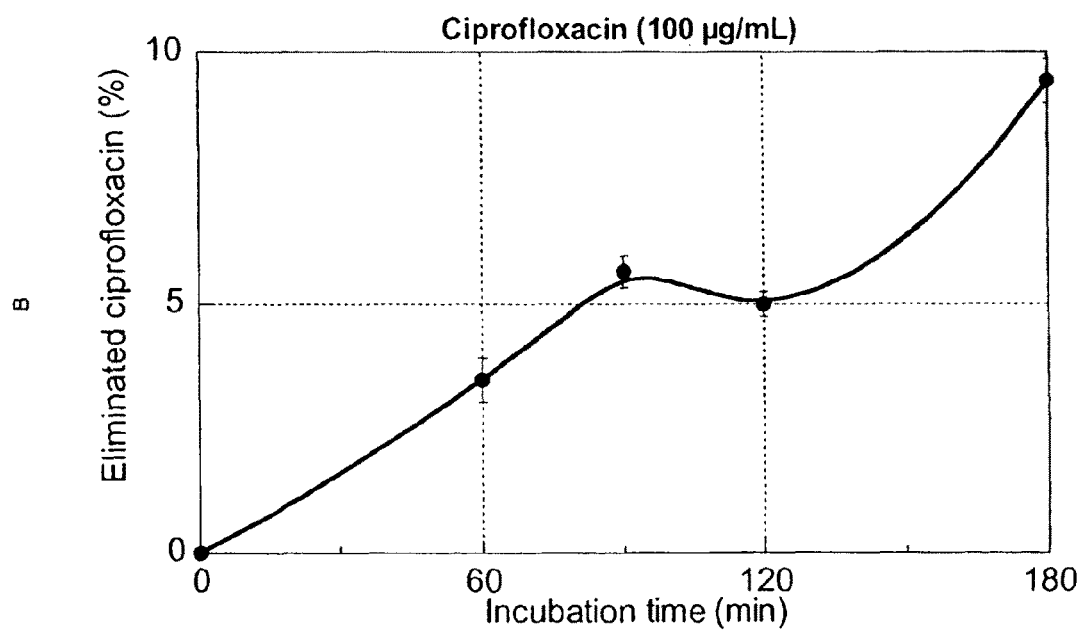
FIG. 15 represents the percentage of ciprofloxacin eliminated by adsorption versus time (min) of incubation with zinc-pectinate beads loaded with activated charcoal and 10% (w/v) Tween 80 (10% w/v of zinc acetate) in the simulated colonic medium. Beads (2 mg/mL (blue circles) are incubated in simulated colonic medium containing an initial ciprofloxacin concentration of 100 µg/mL.

As shown in FIG. 15, ciprofloxacin adsorbs slowly and weakly: only 10% of the initial concentration has adsorbed after 3 hours of incubation even though the activated charcoal has been released from the beads. Ciprofloxacin may be in competition with Tween 80 for adsorption onto activated charcoal.

Experiment 5: Zn-pectinate beads encapsulating activated charcoal were used for this experiment. The activated charcoal to pectin ratio was 5/3 (w/w). Zinc concentration used for ionotropic gelation was 10% (w/v). Beads were formulated with 5% (w/v) Lutrol® F68. Beads were washed three times for 1 minute. The efficiency of the adsorbent to reduce ciprofloxacin concentration after release from the pectin was determined under simulated colonic conditions. The SCM used for this study was the following: HEPES (2.383 g/L) and NaCl (8.474 g/L) solution (pH 6) containing a pectinolytic enzyme solution (Pectinex® SPL Ultra, Sigma, France) (1/5; v/v). Typically, one or two beads were incubated with SCM containing 100 µg/mL of ciprofloxacin (2 mg or 5 mg of beads/mL of SCM).

Beads were incubated in the SCM described above containing ciprofloxacin at 37° C. under gentle tangential stirring. At desired time points samples were centrifuged at 10,000 RPM using a microcentrifuge. The supernatant was filtered on syringe driven filter unit (Millex®-HV, 0.45 µm, PVDF, 4 mm) and analyzed using HPLC.

Figure 16:
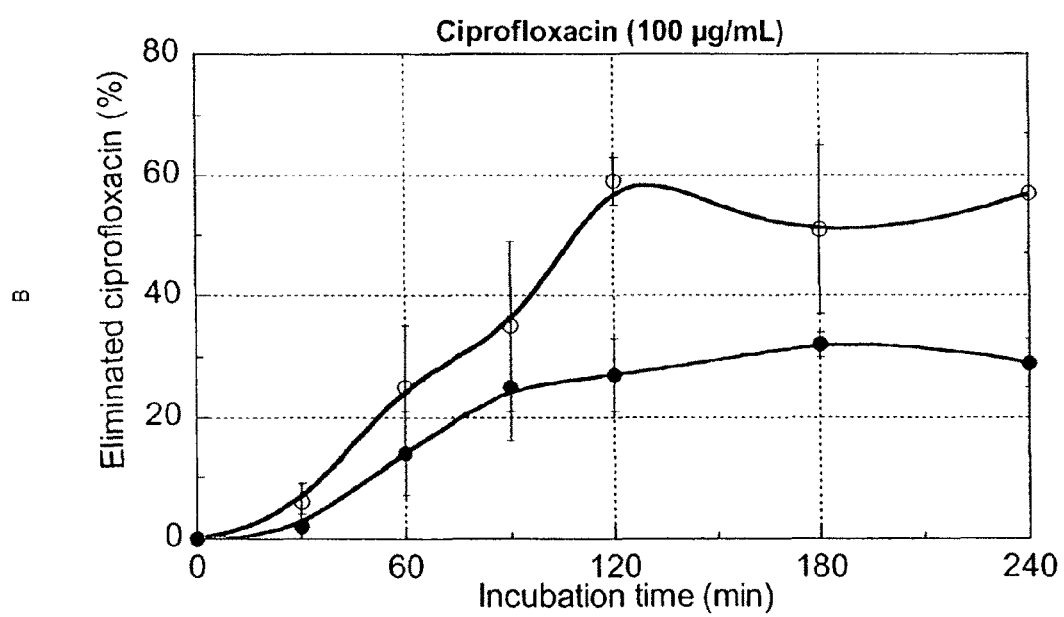
FIG. 16 represents the percentage of ciprofloxacin eliminated by adsorption versus time (min) of incubation with zinc pectinate beads loaded with activated charcoal and 5% (w/v) Lutrol® F68 (10% w/v of zinc acetate). Beads (2 mg/mL (blue filled circles) or 5 mg/mL (black empty circles)) are incubated in SCM containing an initial ciprofloxacin concentration of 100 µg/mL.

As shown in FIG. 16, the amount of ciprofloxacin eliminated by adsorption onto activated charcoal released from Zn-pectinate beads prepared with Lutrol® F68, increases until it reaches a plateau after 2 to 3 hours of incubation, independently of the amount of beads used. Eliminated ciprofloxacin is around 30% and 60% of the initial concentration after 3 hours incubation, for bead concentration of 2 mg/mL and 5 mg/mL SCM, respectively. The adsorption capacity of activated charcoal seems to be affected by the presence of Lutrol® F68.

Experiment 6: Controls for Adsorption of Ciprofloxacin onto Charcoal-Loaded Beads: Adsorption Efficiency in Simulated Colonic Conditions with "Nude Beads"

"Nude beads" were used for these experiments. Ca-pectinate and Zn-pectinate beads were prepared with a 3% (w/v) pectin solution and with 6 and 10% w/v zinc acetate solution respectively, as mentioned for adsorbent-loaded beads. Ciprofloxacin (100 µg/mL) was incubated with "nude beads" under the same experimental conditions that binding tests with loaded-beads. Based on the fact that one charcoal-loaded bead included around 0.5 mg of pectin, control tests were carried out using ciprofloxacin solution in proportion 1 mL/0.5 mg nude beads. Residual antibiotic concentration was determined by using mixed HPLC-UV, as described above. After 3 hours of incubation, ciprofloxacin level in tested samples does not differ from controls (Table 14 and 15). The antibiotic amount remained constant, demonstrating that ciprofloxacin was not adsorbed by the pectin.

TABLE 14

Residual ciprofloxacin concentration after incubation without or with nude calcium-pectinate beads, in SCM (pectinolytic enzymes: 1/20).

| | Ciprofloxacin concentration (µg/mL) | | |
|---|---|---|---|
| Incubation time (min) | 15 | 60 | 180 |
| Controls (without beads) (n = 3) | 95.6 ± 0.1 | 95.7 ± 0.1 | 95.9 ± 0.4 |
| With Ca-pectinate nude beads (n = 3) | 95.50 ± .1 96.2 ± 0.2 | 95.9 ± 0.1 96.6 ± 0.25 | 95.1 ± 0.3 95.3 ± 0.5 |

TABLE 15

Residual ciprofloxacin concentration after incubation without or with nude zinc-pectinate beads, in SCM (pectinolytic enzymes: 1/20).

| | Ciprofloxacin concentration (µg/mL) | | |
|---|---|---|---|
| Incubation time (min) | 30 | 60 | 180 |
| Controls (without beads) (n = 2) | 106 ± 0.1 | 106 ± 0.1 | 107 ± 0.1 |

TABLE 15-continued

Residual ciprofloxacin concentration after incubation without or with nude zinc-pectinate beads, in SCM (pectinolytic enzymes: 1/20).

| | Ciprofloxacin concentration (µg/mL) | | |
|---|---|---|---|
| Incubation time (min) | 30 | 60 | 180 |
| With Zn-pectinate nude beads (n = 2) | 105 ± 0.1 | 104 ± 0.1 | 104 ± 0.1 |

Example 4

Adsorption of *Clostridium difficile* Toxins

Adsorption Efficiency in Simulated Colonic Conditions with Encapsulated Adsorbents

*Clostridium difficile* toxins (A and B) were provided by Sigma-Aldrich (USA). Ca-pectinate beads encapsulating activated charcoal, substantially as described above, were used for this experiment. The activated charcoal to pectin ratio was 5/3 (w/w). The efficiency of the adsorbent at reducing the concentration of *C. difficile* toxins after release from the pectin was determined under simulated colonic conditions.

The SCM used for this study was the following: HEPES (2.383 g/L) and NaCl (8.474 g/L) solution (pH 6) containing a pectinolytic enzyme solution (Pectinex® SPL Ultra, Sigma, France) (1/20; v/v). Beads were incubated in the SCM described above containing *C. difficile* toxins at 37° C. under gentle tangential stirring. At desired time points, samples were centrifuged at 10,000 RPM using a micro-centrifuge. The supernatant was filtered on syringe driven filter unit (Millex®-HV, 0.45 µm, PVDF, 4 mm) and analyzed using an ELISA assay (kit Premier Toxins A&B from meridian Bioscience, Inc. Cincinnati, Ohio).

Rapid adsorption of the toxins incubated in SCM was observed, suggesting that the colonic particulate delivery systems described herein will adsorb bacterial and fungal toxins in the colon, and alleviate symptoms caused by these toxins.

REFERENCES

1. Leonard, F., et al., *Use of beta-lactamase producing anaerobes to prevent ceftriaxone from degrading intestinal resistance to colonization*. J Infect Dis, 1989. 160(2): p. 274-80.
2. Stiefel, U., et al., *Oral administration of beta-lactamase preserves colonization resistance of piperacillin-treated mice*. J Infect Dis, 2003. 188(10): p. 1605-9.
3. Alegakis, A. K., et al., *In vitro study of oxytetracycline adsorption on activated charcoal*. J Environ Sci Health B, 2000. 35(5): p. 559-69.
4. Browne, J. E., et al., *Characterization and adsorptive properties of pharmaceutical grade clays*. J Pharm Sci, 1980. 69(7): p. 816-23.
5. Khalil, S., L. Mortada, and M. El-Khawas, *The uptake of ampicillin and amoxycillin by some adsorbents*. Int. J. Pharm., 1984. 18: p. 157-167.
6. Grant, G., et al., *Biological interactions between polysaccharides and divalent cations: the egg-box model*. FEBS letter, 1973. 32: p. 195-198.

Each document referred to herein is hereby incorporated by reference in its entirety for all purposes.

Having hereby disclosed the subject matter of the present invention, it should be apparent that many modifications, substitutions, and variations of the present invention are possible in light thereof. It is to be understood that the present invention can be practiced other than as specifically described. Such modifications, substitutions and variations are intended to be within the scope of the present application.

What is claimed is:

1. A method of inactivating substances either present in the colon, or as they reach the colon, comprising administering an orally administrable particulate drug delivery system to a patient in need thereof,
    wherein the drug delivery system comprises an adsorbent encapsulated into a polymer selected from the group consisting of chitosan, alginates, xanthan, curdlan, guar gum, polysaccharides, and polymethylmethacrylate polymers, and
    wherein the substances that are adsorbed are selected from the group consisting of antibiotics, chemicals, allergens, toxins and pharmaceutical agents known to cause side effects when they reach the colon, and
    wherein the delivery system delivers the adsorbent to the colon site.
2. The method of claim 1, wherein the polymethacrylate polymer is a Eudragit® polymer.
3. The method of claim 1, wherein the polysaccharide is an ionically crosslinkable polysaccharide.
4. The method of claim 3, wherein the ionically-crosslinkable polysaccharide is pectin, and wherein the pectin is crosslinked with a metal cation.
5. The method of claim 1, wherein the particle is reticulated with a polymer.
6. The method of claim 5, wherein the polymer is a polymethylmethacrylate polymer, polyethyleneimine, chitosan, or polylysine.
7. The method of claim 1, wherein the adsorbent is selected from the group consisting of activated charcoal, clays, talc, silica, and resins.
8. The method of claim 1, wherein the clay is selected from the group consisting of bentonite, kaolin, montmorrillonite, attapulgite, halloysite, and laponite.
9. The method of claim 1, wherein the silica is selected from the group consisting of colloidal silica, mesoporous silica, fumed silica and zeolites.
10. The method of claim 4, wherein the pectin is amidated pectin.
11. The method of claim 1, wherein the drug delivery system further comprises an enzyme that inactivates an antibiotic.
12. The method of claim 1, wherein the drug delivery system is administered to a patient, either before, during, or after administration of an antibiotic.
13. The method of claim 1, wherein the administration of the drug delivery system treats or prevents adverse effects of an antibiotic to the intestinal flora.
14. The method of claim 1, wherein the administration of the drug delivery system treats or prevents adverse effects of a bacterial or fungal toxin on the intestinal flora.
15. The method of claim 1, wherein the administration of the drug delivery system treats or prevents adverse effects of a pharmaceutically active agent which has beneficial effects when it interacts with receptors outside of the colon, but has adverse side effects when it interacts with receptors inside the colon.
16. A drug delivery system for oral administration, and colonic release of adsorbents, comprising:

a) an adsorbent capable of adsorbing an antibiotic, a bacterial or fungal toxin, or a pharmaceutically active agent known to cause adverse side effects when they reach the colon, and
b) a drug delivery device comprising particles formed from one or more of chitosan, alginates, xanthan, curdlan, guar gum, polysaccharides, or polymethylmethacrylate polymers.

17. The drug delivery system of claim 16, where the polysaccharide is an ionically crosslinkable polysaccharide.

18. The drug delivery system of claim 17, wherein the ionically crosslinkable polysaccharide is pectin.

19. The drug delivery system of claim 16, wherein the drug delivery system is capable of being sufficiently degraded in the colon to release an effective amount of the adsorbent.

20. The drug delivery system of claim 16, wherein the particles are reticulated with a polymer.

21. The drug delivery system of claim 20, wherein the polymer is polyethyleneimine, chitosan, polylysine, or polymethylmethacrylate polymer.

22. The drug delivery system of claim 16, wherein the adsorbent is selected from the group consisting of activated charcoal, clays, talc, silica, and resins.

23. The drug delivery system of claim 22, wherein the clay is selected from the group consisting of bentonite, kaolin, montmorrillonite, attapulgite, halloysite, and laponite.

24. The drug delivery system of claim 22, wherein the silica is selected from the group consisting of colloidal silica, mesoporous silica, fumed silica and zeolites.

25. The drug delivery system of claim 16, wherein the pectin is amidated pectin.

26. The drug delivery system of claim 16, further comprising an enzyme that inactivates an antibiotic.

* * * * *